United States Patent [19]

Shirasaki

[11] Patent Number: 5,156,158
[45] Date of Patent: Oct. 20, 1992

[54] ELECTRONIC BLOOD PRESSURE METER

[75] Inventor: Osamu Shirasaki, Hyogo, Japan

[73] Assignee: Omrom Corporation, Kyoto, Japan

[21] Appl. No.: 528,980

[22] Filed: May 25, 1990

[30] Foreign Application Priority Data

May 25, 1989 [JP] Japan ................. 1-131842
May 29, 1989 [JP] Japan ................. 1-135382
Jun. 5, 1989 [JP] Japan ................. 1-142560

[51] Int. Cl.$^5$ .................................. A61B 5/02
[52] U.S. Cl. ........................ 128/680; 128/677; 128/687
[58] Field of Search ............ 128/672, 677, 680, 681, 128/687, 688, 689

[56] References Cited

U.S. PATENT DOCUMENTS 4,644,152 10/1987 Link ................. 128/677
4,718,426 1/1988 Russell ............. 128/677
4,830,019 5/1988 Shiranski .......... 128/680

Primary Examiner—Kyle L. Howell
Assistant Examiner—Scott R. Akers
Attorney, Agent, or Firm—Fish & Richardson

[57] ABSTRACT

An electronic blood pressure meter, comprising: a cuff adapted to be placed on a subject person; a pressurizing pump for pressurizing air inside the cuff; a vent valve for removing air from the cuff; a pressure sensor for detecting air pressure in the cuff; cardiovascular information detector for detecting cardiovascular information on the subject person from the pressure sensor and computing a parameter from the cardiovascular information; a membership function storage unit storing a plurality of membership functions using a relative pressure of the air pressure in the cuff to a blood pressure value as its input variable; a membership function selecting unit for selecting one of the membership functions corresponding to the parameter from the membership functions stored in the membership function storage unit; and a control unit for controlling operation of the electronic blood pressure meter according to the membership functions. Thus, blood pressure measurement can be completed in a very short time period, and it is also possible to detect insufficiency of initial cuff pressurization and the extent of insufficiency immediately after starting the measurement.

5 Claims, 21 Drawing Sheets

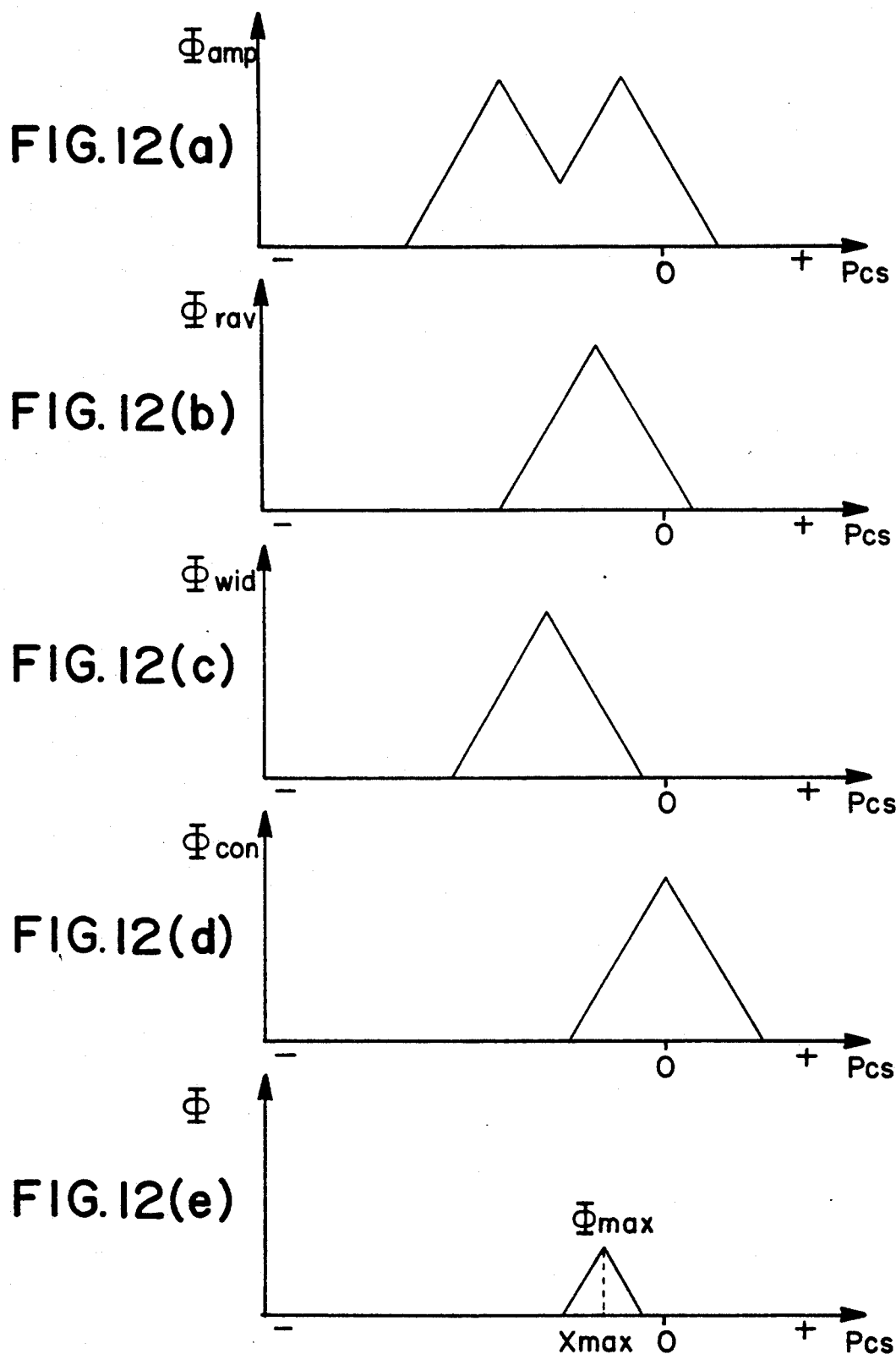

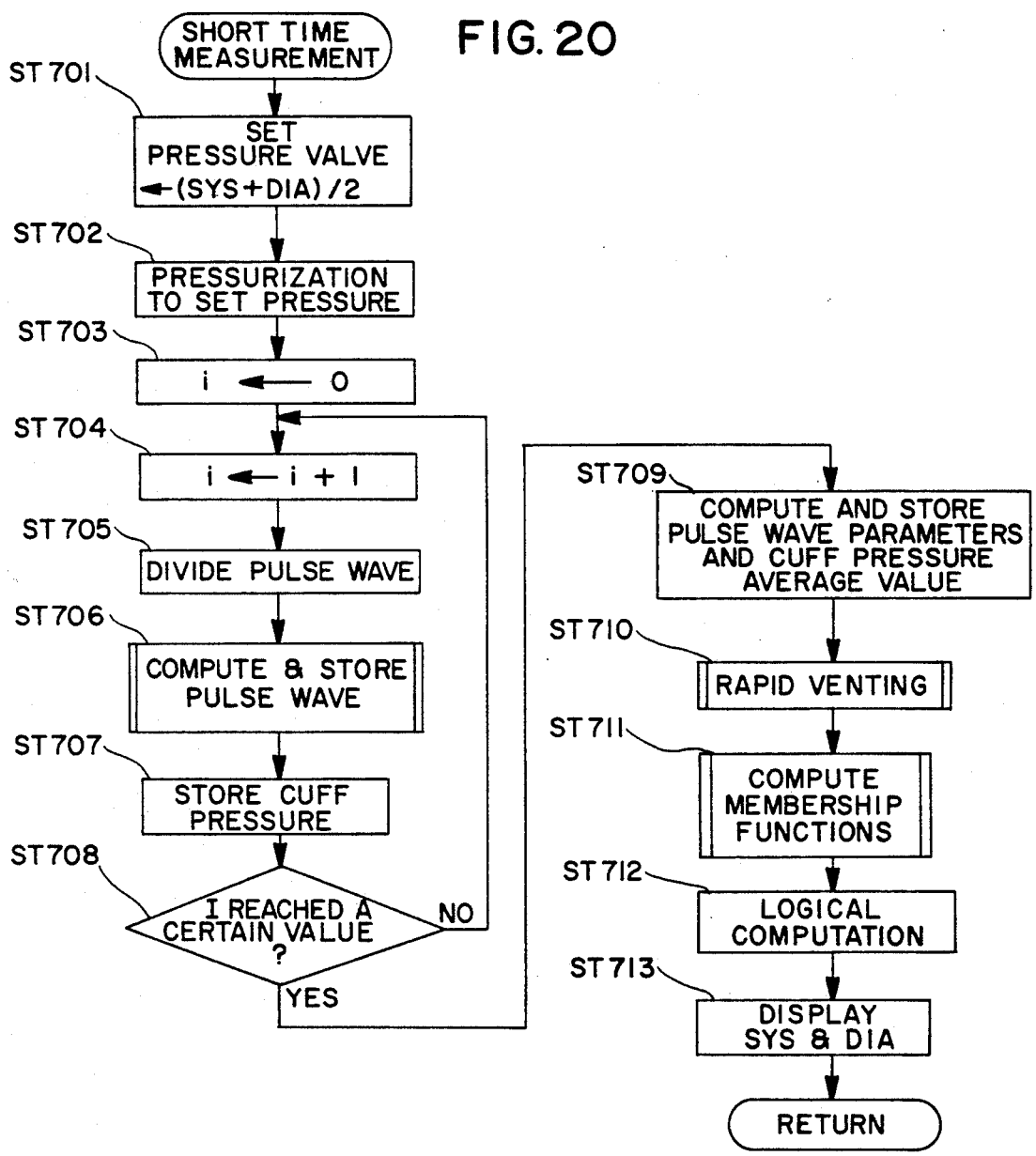

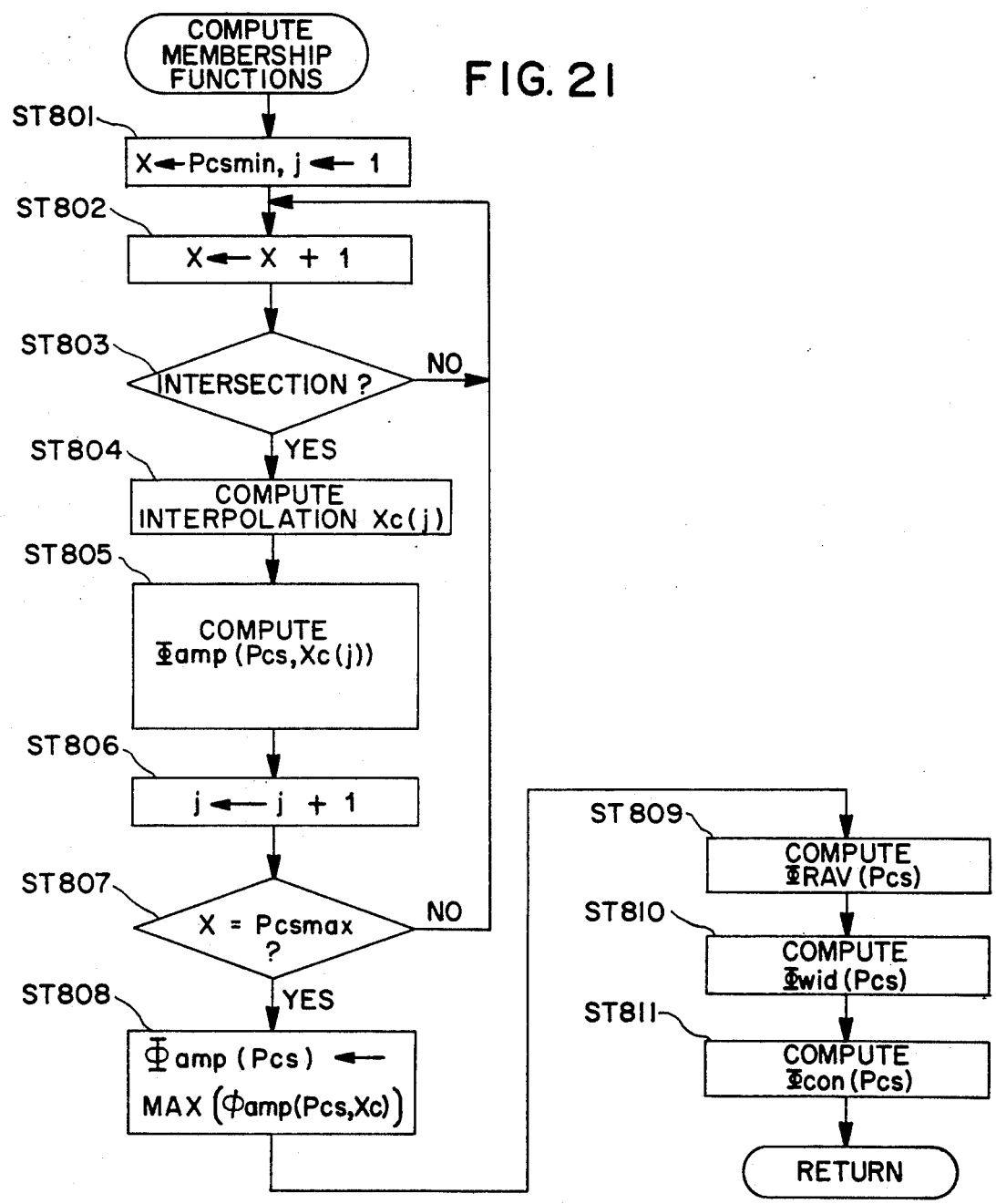

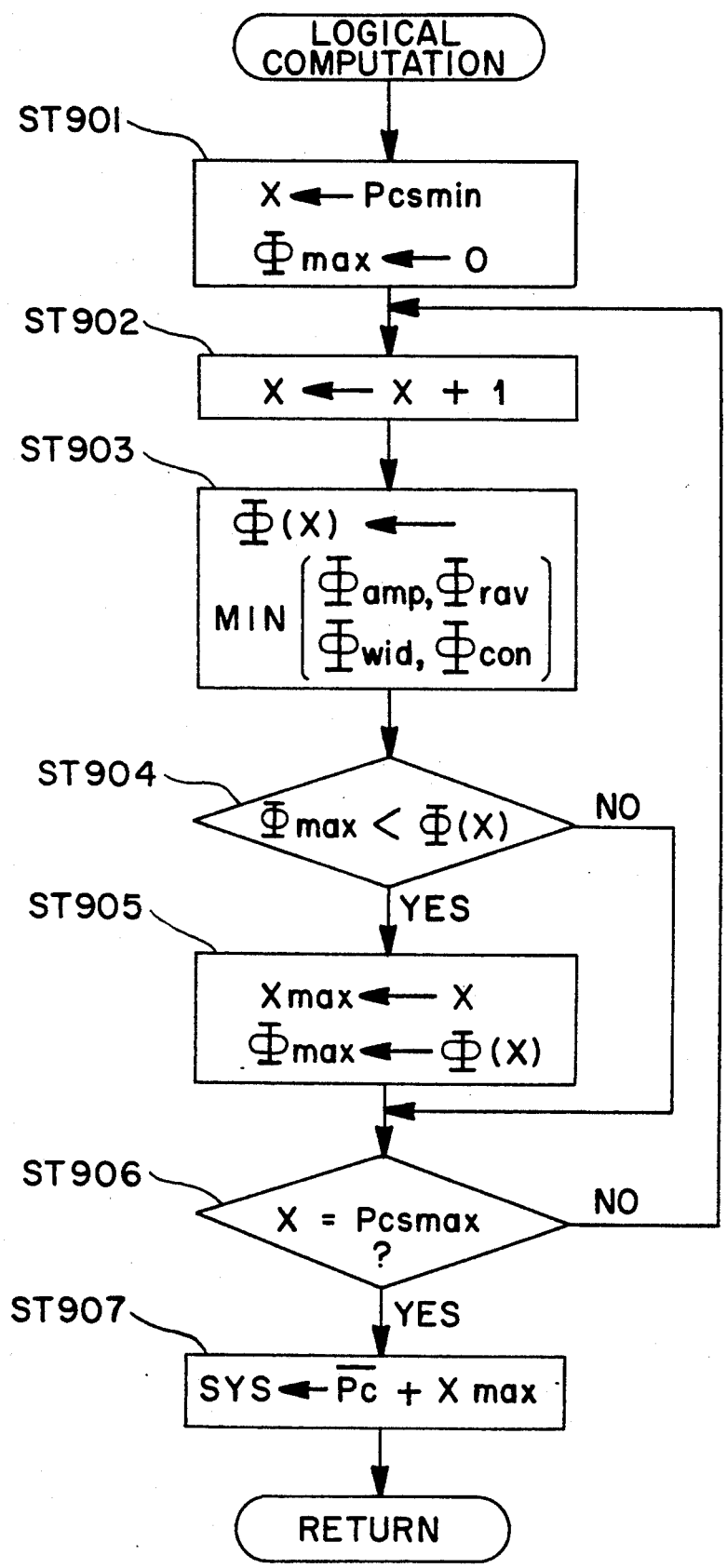

ELECTRONIC BLOOD PRESSURE METER

TECHNICAL FIELD

The present invention relates to an electronic blood pressure meter, and in particular to an electronic blood pressure meter which is capable of measuring systolic and diastolic blood pressure values in a very short time. The present invention also relates to an electronic blood pressure meter which may be used as a continuous blood pressure monitoring device, and in particular to such a device which is highly accurate and minimizes discomfort to the patient on whom the device is used.

BACKGROUND OF THE INVENTION

As conventional electronic blood pressure meters, there are known those using a cuff wrapped around an upper arm of the subject person for measurement. According to such an electronic blood pressure meter, the air pressure in the cuff (simply referred to as cuff pressure hereinafter) is changed at a predetermined rate, and cardiovascular information obtained during this process (pulse wave, Korotkoff sound, etc.) is used to determine the systolic and diastolic (or maximum and minimum) blood pressure values.

The electronic blood pressure meters based on this principle may be classified into those based on the oscillometric method utilizing pulse wave as the cardiovascular information and the Korotkoff method using the Korotkoff sound as the cardiovascular information. An electronic blood pressure meter based on the oscillometric method detects pulse wave during the process of gradual venting the cuff, and determines diastolic and systolic blood pressure values (which are simply referred to as blood pressure values hereinafter) by evaluating the changes in the amplitude of the pulse wave. On the other hand, an electronic blood pressure meter based on the Korotkoff method detects the Korotkoff sound with a microphone during the process of gradual venting to determine blood pressure values.

In either case, it is necessary to increase the air pressure in the cuff (cuff pressure) above the systolic pressure before measurement can be started, and it is in principle not possible to determine blood pressure values if pressurization is not sufficient or the set pressure is lower than the systolic blood pressure.

According to an electronic blood pressure meter based on the oscillometric method, insufficient pressurization cannot be discovered until a late stage of measurement is reached. Therefore, measurement is continued for some time even when pressurization is insufficient only to find out that the pressurization was insufficient after elapsing a certain time period, and measurement has to be started all over again.

On the other hand, according to an electronic blood pressure meter based on the Korotkoff method, it is possible to discover insufficient pressurization by presence or absence of the Korotkoff sound immediately after starting measurement. However, it cannot be found how insufficient pressurization was, and repressurization by a certain amount may turn out to be insufficient again or an excessive pressurization may take place. Furthermore, because of the use of a highly sensitive microphone, unnecessary repressurization may be made by mistaking surrounding noises for the Korotkoff sound, and unnecessary repressurization may be carried out therefor.

Thus, the conventional electronic blood pressure meter involves the inconvenience that the set value of pressurization must be carefully determined so as to avoid insufficient pressurization, and may cause undue pain and obstruction of blood flow to the subject person by failure to effect a successful completion of a measurement process due to insufficient pressurization. Further, the need for repeated measurement reduces the efficiency of the measurement process.

Generally speaking, a gravely ill patient or a patient during operation requires not only a quick measurement of his blood pressure but also a blood pressure measurement method which is capable of detecting rapid changes in his blood pressure. To meet this need, the method called as the direct method is generally employed for such a purpose. According to this method, a needle is inserted into an artery of the patient, and the internal pressure of the artery is directly measured with a pressure sensor connected thereto and continually displayed. However, this method is not only inconvenient to carry out but also presents the risks of infection and inflicting injury to the patient.

Therefore, lately, there has been introduced the continuous blood pressure monitoring device which carries out the aforementioned indirect measuring process in an intermittent and automatic fashion, the indirect measuring process consisting of the steps of placing a cuff on an upper arm of the patient, increasing and reducing the air pressure in the cuff (which may be referred to as cuff pressure hereinafter) at a fixed rate, and determining blood pressure values according to cardiovascular information such as the Korotkoff sound and the pulse wave obtained during this process. This continuous blood pressure monitoring device is safer and simpler than those using the direct method since all that is necessary is to place a cuff on the subject person.

However, according to such a continuous blood pressure monitoring device, since it is necessary to change the cuff pressure over a range covering the systolic blood pressure value and the diastolic blood pressure value, each measurement process takes from several seconds to more than one minute, and it is difficult to detect rapid changes in the blood pressure.

Further, according to such a continuous blood pressure monitoring device, since the blood flow in the artery must be temporarily obstructed by the cuff, if the measurement is repeated without interruption, the resulting blockage of blood flow prevents accurate measurement, and an undesirable effect may be caused to a patient having a problem with his blood circulation.

Further, if the blood pressure measurement takes place during the process of reducing the cuff pressure, since it is necessary to increase the cuff pressure above the systolic blood pressure before reducing the cuff pressure, any insufficiency of initial pressurization prevents accurate blood pressure measurement, and repeated measurement becomes necessary. For such reasons, the direct method is still widely used for continuous monitoring of blood pressure.

BRIEF SUMMARY OF THE INVENTION

In view of such problems of the prior art, a primary object of the present invention is to provide an electronic blood pressure meter which is capable of quick measurement of blood pressure and relatively free from the problem of measurement failures due to insufficient pressurization.

A second object of the present invention is to provide an electronic blood pressure meter which allows not only insufficient pressurization to be quickly discovered but also the extent of the insufficiency of pressurization to be known.

A third object of the present invention is to provide a continuous blood pressure monitoring device which substantially reduces the time period required for blood pressure measurement, which is capable of detecting rapid changes in blood pressure, which prevents blockage of blood flow, which is capable of accurate blood pressure measurement, and which is free from the problem of the need for repeated measurement due to insufficient initial pressurization.

These and other objects of the present invention can be accomplished by providing an electronic blood pressure meter, comprising: a cuff adapted to be placed on a subject person; pressure adjusting means for adjustably pressurizing air inside the cuff; venting means for removing air from the cuff; pressure detecting means for detecting air pressure in the cuff; cardiovascular information detecting means for detecting cardiovascular information such as pulse wave on the subject person from the pressure detecting means and computing a parameter from the cardiovascular information; membership function storage means storing a plurality of membership functions using a relative pressure of the air pressure in the cuff to a blood pressure value as its input variable; membership function selecting means for selecting one of the membership functions corresponding to the parameter from the membership functions stored in the membership function storage means; and control means for controlling operation of the electronic blood pressure meter according to the membership functions.

According to a preferred embodiment of the present invention, the control means comprises blood pressure determining means for estimating the aforementioned relative pressure by carrying out a certain arithmetic operation on the membership function for the parameter selected by the membership function selecting means, and determining a blood pressure value.

Now the function of the electronic blood pressure meter of the present invention is described in the following with reference to FIGS. 1, 2 and 9. The waveform of pulse wave is known to change with cuff pressure. It is therefore expected to be able to estimate how far the current cuff pressure is away from the systolic blood pressure, or to know the relative pressure, from the pulse waveform.

To evaluate the pulse waveform, such parameters as the pulse wave amplitude AMP, the pulse wave integration level RAV, the pulse wave width ratio WID, and the degree of curving CON may be computed as shown in FIG. 2. Now, let us consider the pulse wave amplitude AMP. In FIG. 9(a) is plotted the relationship between the pulse wave amplitude AMP and the relative cuff pressure Pc' obtained from a large number of subject persons. FIG. 9(a) essentially shows a probability density distribution using the pulse wave amplitude AMP and the relative cuff pressure Pc' as variables, and it may be used to generate membership functions.

When the pulse wave amplitude is actually measured, and FIG. 9(a) is cut through by this pulse wave amplitude AMP*, its cut surface becomes as indicated by FIG. 1(a), and it amounts to a probability density distribution of the relative cuff pressure Pc' with respect to the pulse wave amplitude. Such membership functions can be obtained in the same manner for each of the other parameters (refer to FIGS. 1(b), 1(c) and 1(d)). A function obtained by carrying out a predetermined logical operation such as multiplication and addition on these membership functions related to the associated parameters is given, for instance, by the graph shown in FIG. 1(e), and it can be estimated that the relative cuff pressure corresponding to the maximum value of this function is a most probable value. Once the relative cuff pressure is estimated, it becomes readily possible to compute the systolic (or diastolic) blood pressure value from the relative cuff pressure and the current cuff pressure.

The blood pressure values may be thus determined from the pulse wave parameters, and, since detection of only one cycle is sufficient for measurement in theory, the time interval required for measurement can be reduced, and rapid changes in blood pressure values can be detected. There is no change in the need for pressurizing the cuff in detecting pulse wave, but measurement failure due to insufficient cuff pressurization will rarely occur because the cuff pressure needs to be only so high as to permit detection of pulse wave.

According to another preferred embodiment of the present invention, the control means comprises pressurization insufficiency detecting means for estimating the aforementioned relative pressure by carrying out a certain arithmetic operation on the selected membership function for the parameter, and detecting an insufficiency in cuff pressurization from this estimated relative pressure. Thus, it becomes possible to know not only the occurrence of insufficiency in pressurization but also how insufficient it is.

According to a third preferred embodiment of the present invention, aid control means comprises first blood pressure determining means for determining a blood pressure value according to the cardiovascular information obtained by the cardiovascular information detecting means and the air pressure detected by the pressure detecting means during the process of changing the air pressure in the cuff with the pressure adjusting means; pulse wave parameter characteristics storage means for storing a relationship between a pulse wave parameter obtained by the cardiovascular information detecting means and a blood pressure value determined by the first blood pressure value determining means with respect to pulse wave detected by the cardiovascular information detecting means during a process of determining a blood pressure value with the first blood pressure determining means; and second blood pressure determining means for computing the parameter with the cardiovascular information detecting means for one of a plurality of cycles of the pulse wave detected by the cardiovascular information detecting means after raising the air pressure in the cuff to a predetermined pressure value with the pressure adjusting means, comparing the parameter with an associated parameter stored in the pulse wave parameter characteristics storage means, and determining blood pressure values according to a predetermined logical operation on a result of the comparison.

According to the continuous blood pressure measuring device of this invention, the waveform of pulse wave may be evaluated in terms of a plurality of parameters such as the pulse wave amplitude, the pulse wave integrated level, the pulse wave width ratio and the degree of curving. Determination of blood pressure values is carried out during the process of reducing or increasing the cuff pressure in the same manner as the conventional methods, and the pulse wave detected during this process is utilized for computing pulse wave parameters so that the pulse wave parameters may be stored in association with the determined blood pressure values.

Once the relationship between the pulse wave parameters and the blood pressure values are stored, it suffices in the subsequent processes to detect a single cycle of pulse wave and the cuff pressure associated therewith to compute the pulse wave parameters and determine the blood pressure values by applying a certain logical operation on the obtained relationship.

Thus, since the continuous blood pressure monitoring device of the present invention requires only a single cycle of pulse wave in principle, it is possible to substantially reduce the time period required to carry out a measurement process so that not only detection of rapid changes in blood pressure is made possible but also an accurate blood pressure measurement is made possible by avoiding the blockage of the blood flow of the patient. It is necessary to pressurize the cuff but the pressure is only required so high as to permit detection of pulse wave without requiring the pressure level to be accurately selected, and the possibility of the measurement failures due to insufficient pressurization is substantially eliminated.

BRIEF DESCRIPTION OF THE DRAWINGS

Now the present invention is described in the following with reference to the appended drawings, in which:

FIGS. 12(a) through 12(e) show an example of membership function for the continuous blood pressure monitoring device of the present invention;

FIG. 20 is a flow chart describing the process of short time measurement in the continuous blood pressure monitoring device of the present invention;

FIG. 21 is a flow chart showing the process of computing the membership functions in the continuous blood pressure monitoring device; and FIG. 22 is a flow chart showing the logical computation process of the continuous blood pressure monitoring device.

DETAILED DESCRIPTION OF THE PREFERRED EMBODIMENTS

Figure 5:
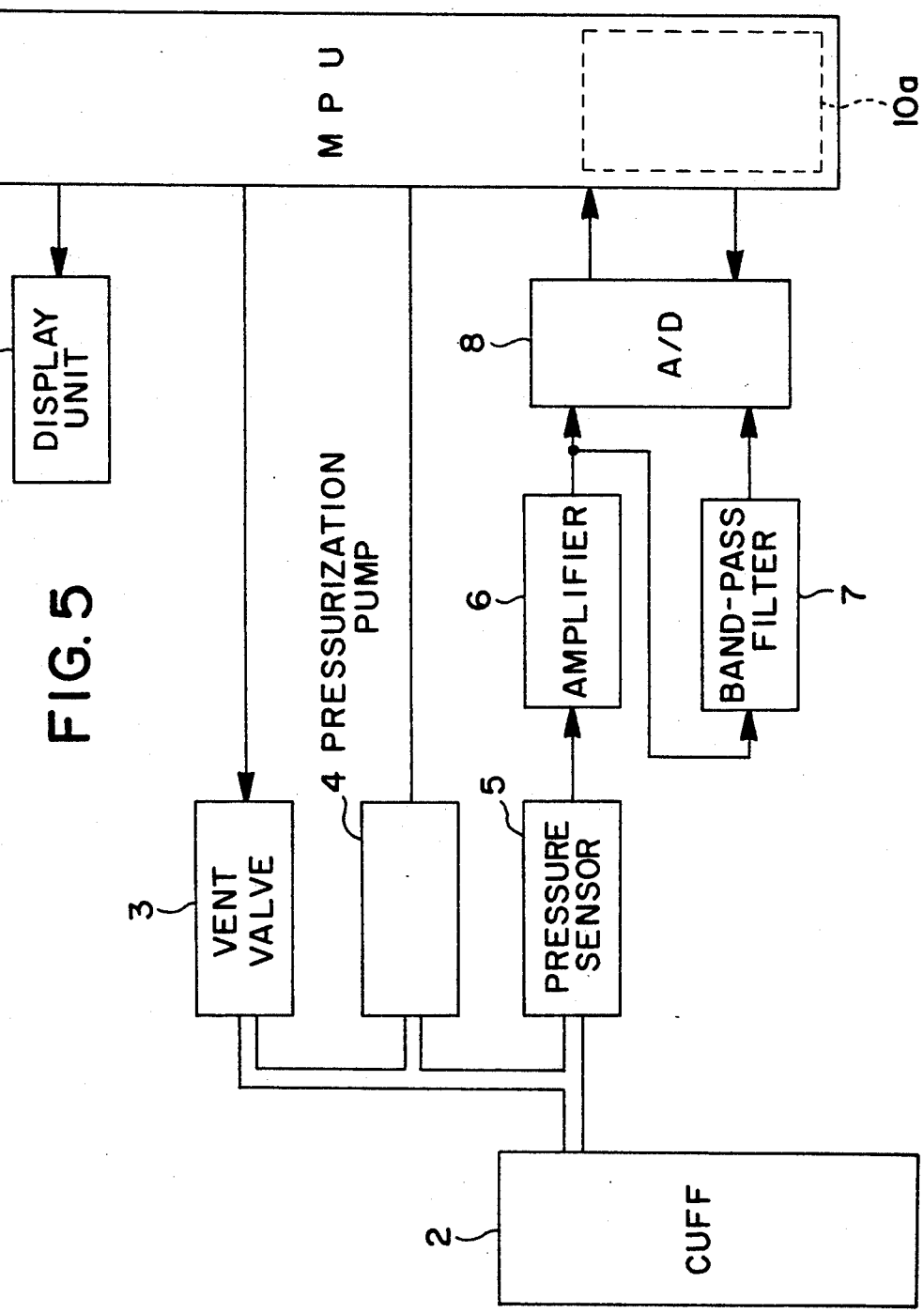
FIG. 5 is a block diagram showing the structure of the electronic blood pressure meter.

FIG. 5 is a block diagram describing the structure of a first embodiment of the electronic blood pressure meter according to the present invention. Numeral 2 denotes a cuff which is to be placed upon an upper arm of a subject person, and this cuff 2 is connected to a vent valve 3, a pressurization pump (pressurization means) 4, and a pressure sensor (pressure detecting means) 5. The vent valve 3 and the pressurization pump 4 are controlled by an MPU 10. The output signal of the pressure sensor 4 (which is referred to as cuff pressure signal hereinafter) is amplified by an amplifier 6, and is then supplied to an analog/digital (A/D) converter 8 to be converted into a digital signal which is then supplied to the MPU 10. The cuff pressure signal is supplied also to a bandpass filter 7 to discriminate a pulse wave signal. This pulse wave signal is also converted into a digital signal by the A/D converter 8, and is then supplied to the MPU 10.

The MPU 10 is provided with the function to compute parameters from the pulse waveform, the function to select membership functions according to the computed parameters, and the function to determine blood pressure values by carrying out a logical operation on the selected membership functions.

The MPU 10 stores a data table for the membership functions and operation programs in its memory 10a. The MPU 10 is connected to a display unit 9 to display various pieces of information such as determined blood pressure values.

Figure 6:
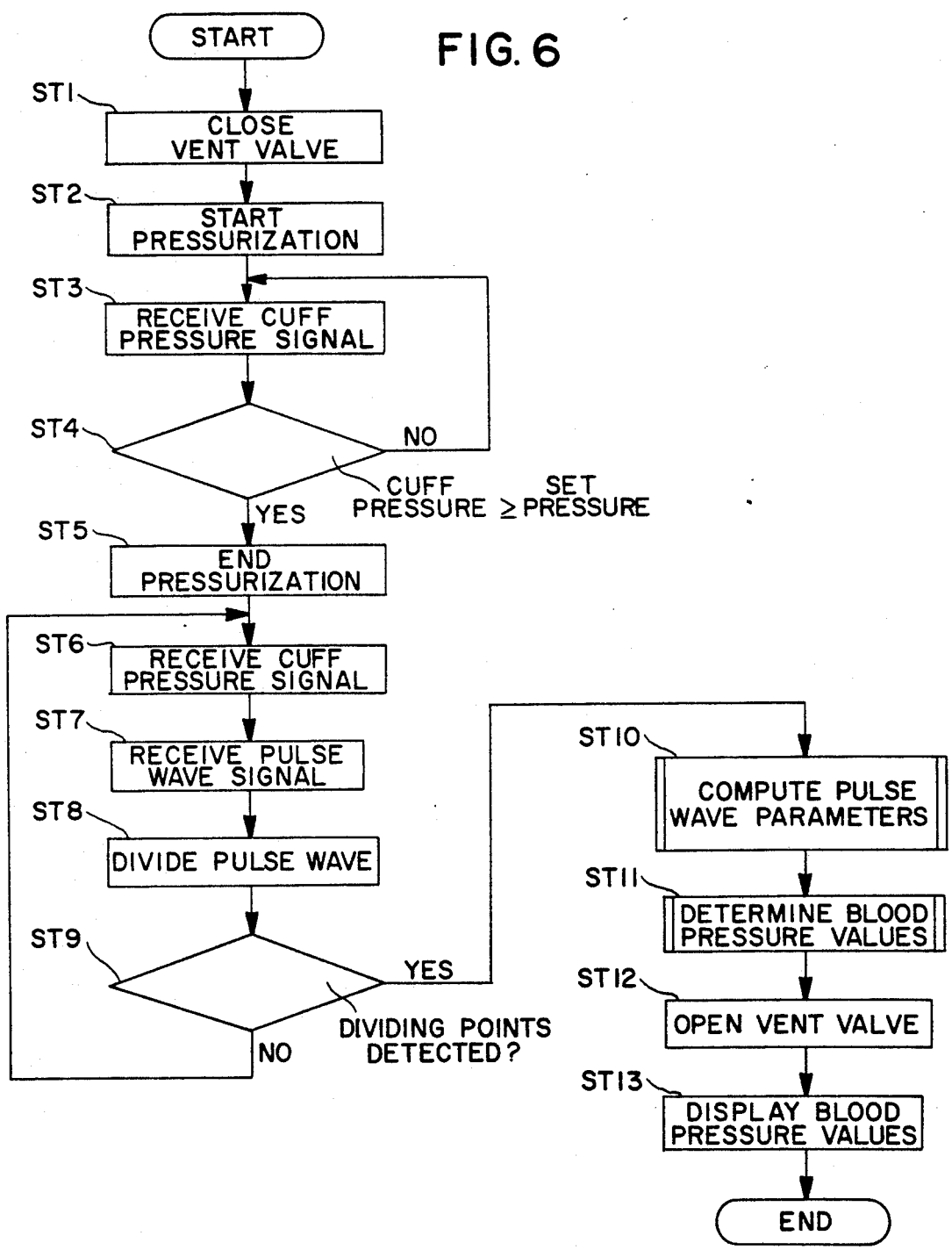
FIG. 6 is a flow chart showing the overall operation of the electronic blood pressure meter.

Now the overall operation of this electronic blood pressure meter is described in the following with reference to FIGS. 3, 4 and 6.

First of all, the cuff 2 is wrapped around an upper arm of a subject person, and a process of blood pressure measurement is started. The MPU 10 turns on the pressurization pump 4 (ST 2, "1" in FIG. 3) with the vent valve 3 closed to start the process of pressurization (step 1 or ST 1, refer to FIG. 6). The MPU 10 receives the cuff pressure signal from the A/D converter 8 (ST 3), and determines if the current cuff pressure has reached a predetermined set pressure value PcO (ST 4). If the result of this determination process is NO, the system flow branches off to ST 3. If the result is YES, the program flow branches off to ST 5. In other words, the processes in ST 3 and ST 4 are repeated until the current cuff pressure reaches the set pressure value PcO. This set pressure value PcO is preferred to be lower than the systolic blood pressure but higher than the diastolic blood pressure, but may not be precise.

Figure 3:
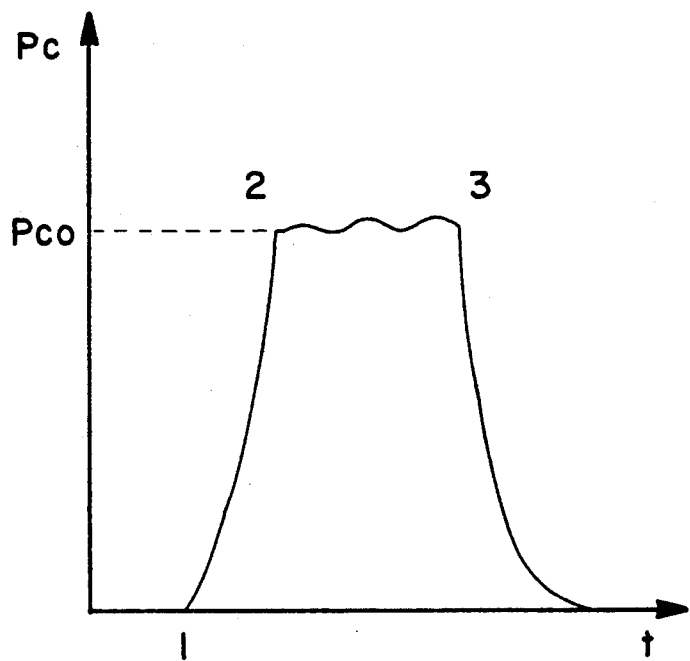
FIG. 3 is a time chart showing the relationship between the cuff pressure and the elapsed time to described the overall operation of the electronic blood pressure meter.
Figure 4:
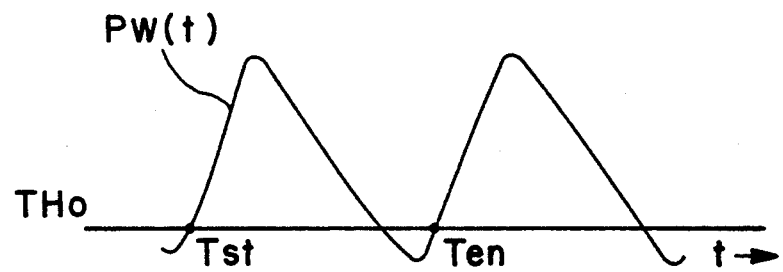
FIG. 4 is a waveform diagram showing the process of dividing the pulse wave in the electronic blood pressure meter.

In ST 5, the MPU 10 stops the pressurization pump 4 ("2" in FIG. 3). The MPU 10 then receives the cuff pressure signal (ST 6) and the pulse wave Pw(t) (ST 7). The MPU 10 slices the pulse wave (ST 8) by applying a threshold value TH0 to this pulse wave Pw(t) as shown in FIG. 4. The MPU 10 then determines if dividing points Tst and Ten have been detected from the pulse wave Pw(t) (ST 9), and if the determination result is NO the system flow branches off to ST 6. Otherwise, the system flow branches off to ST 10. In other words, the processes in ST 5 through ST 9 are repeated until one cycle of pulse wave is obtained.

In ST 10, the MPU 10 computes the pulse wave parameters AMP, RAV, WID and CON, and determines blood pressure values according these parameters (ST 11). More detailed description of the processes in ST 10 and 11 is given hereinafter.

In ST 12, the MPU 10 opens the vent valve 3, and reduces the cuff pressure to zero ("3" in FIG. 3), and displays the blood pressure values determined in ST 11 on the display unit 9 (ST 13) before concluding the measurement. The parameters were computed after detecting a full cycle of pulse wave according to the above described embodiment, but an even higher reliability can be obtained by detecting a number of cycles of pulse wave and taking average values of parameter values obtained from different cycles of the pulse wave.

Figure 7:
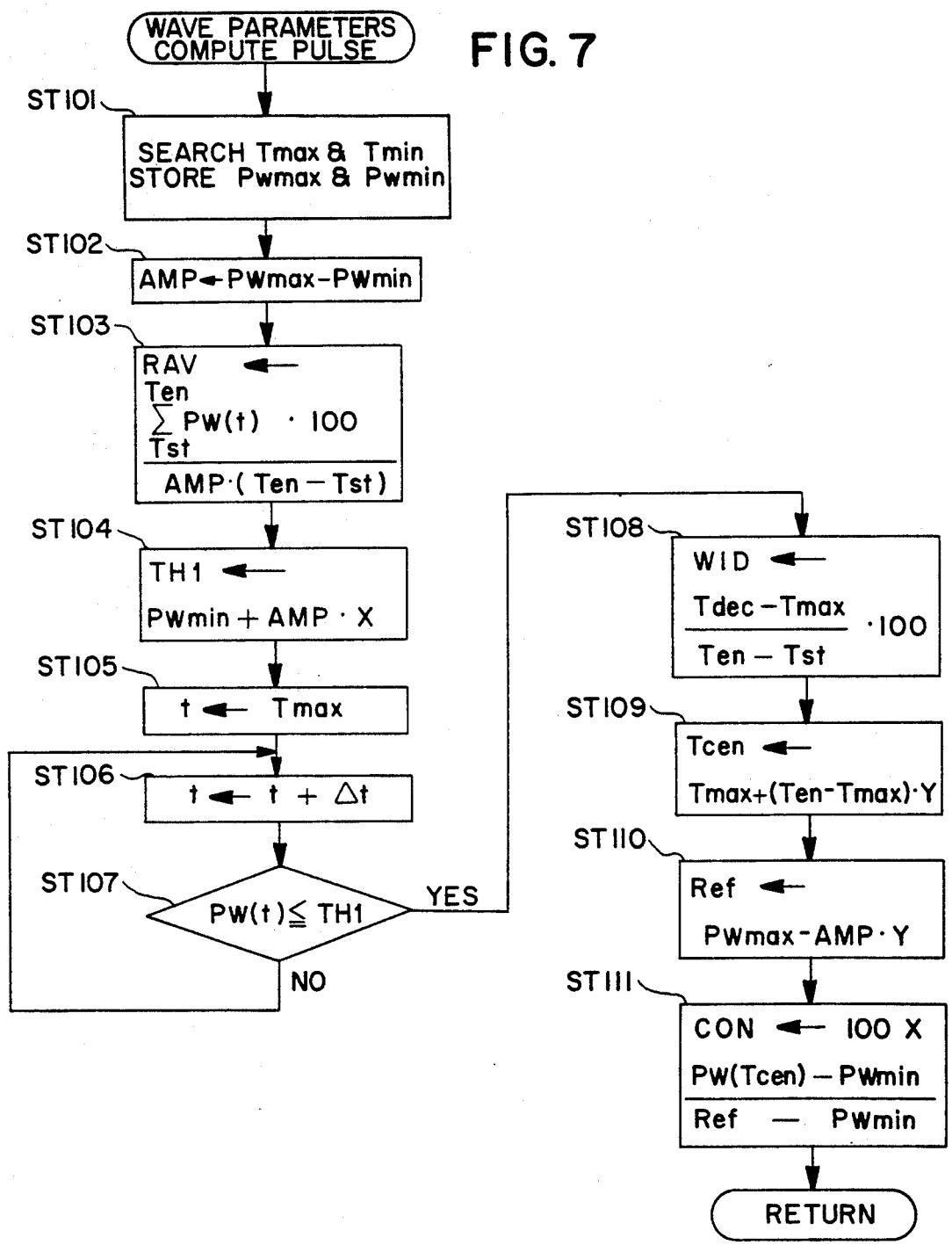
FIG. 7 is a flow chart describing the process of computing the pulse wave parameters in the electronic blood pressure meter.

Now the process of computing the pulse wave parameters (ST 10) is described in the following with reference to FIGS. 2 and 7.

In the electronic blood pressure meter of this embodiment, the pulse wave parameters consist of the pulse wave amplitude AMP, the integrated level RAV, the pulse wave width ratio WID and the degree of curving CON. Of course, the pulse wave parameters are not limited to these four parameters.

Figure 1A:
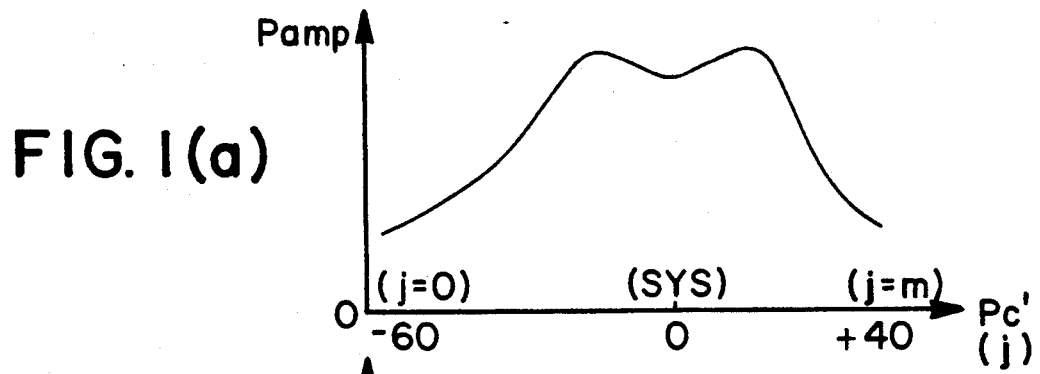
FIGS. 1(a) through 1(e) shows graphs of membership functions for describing the process of determining blood pressure values in the electronic blood pressure meter according to an embodiment of the present invention.
Figure 1B:
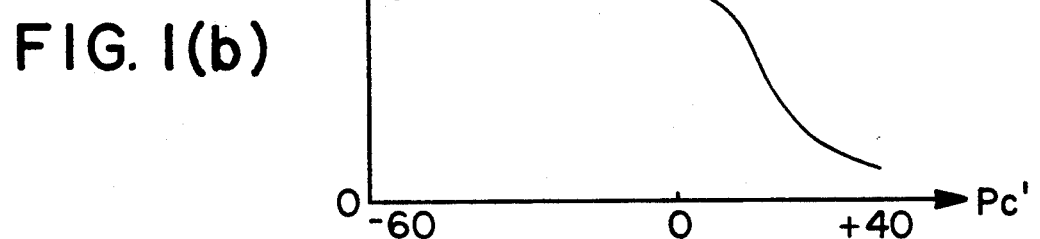
Figure 1C:
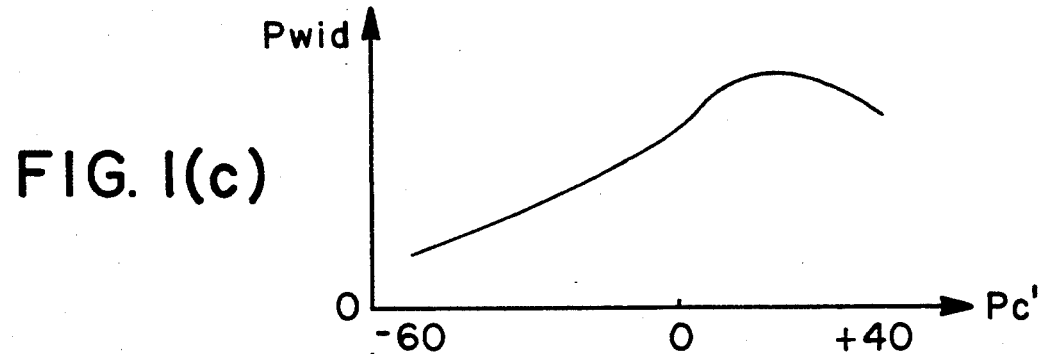
Figure 1E:
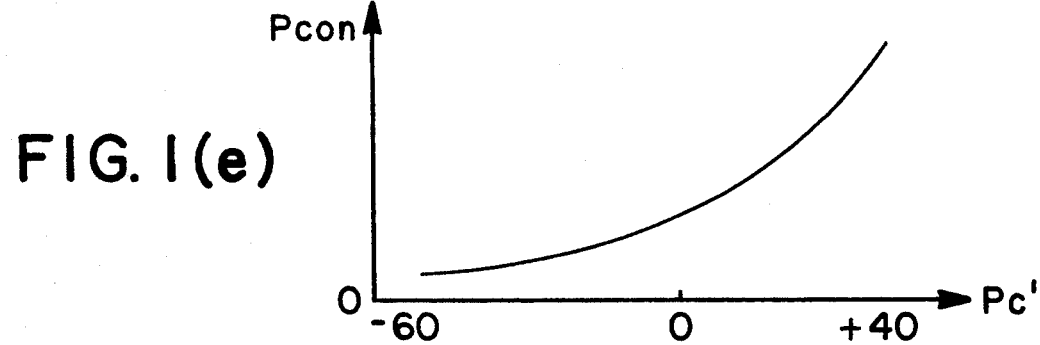
Figure 1D:
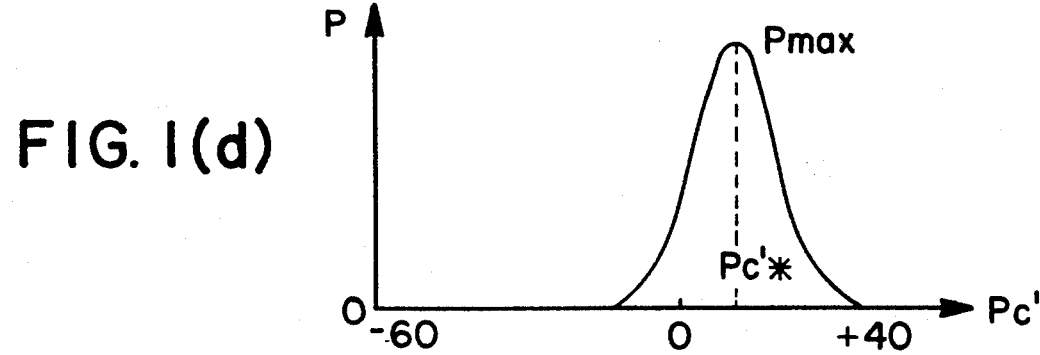
Figure 2A:
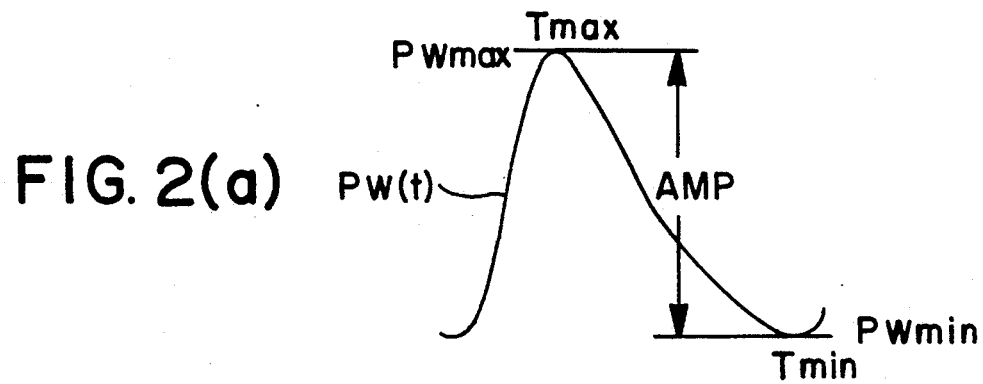
FIGS. 2(a) through 2(d) are waveform diagrams for describing the process of computing the pulse wave parameters in the electronic blood pressure meter.

First of all, the MPU 10 searches for the time points Tmax and Tmin at which the pulse wave Pw(t) takes the maximum and minimum values, respectively, and stores the pulse wave maximum value Pwmax and the pulse wave minimum value Pwmin corresponding to the time points Tmax and Tmin, respectively, in its memory 10a (ST 101, refer to FIG. 2(a)). Then, Pwmin is subtracted from Pwmax, and the pulse wave amplitude AMP is thereby obtained (ST 102).

Figure 2B:
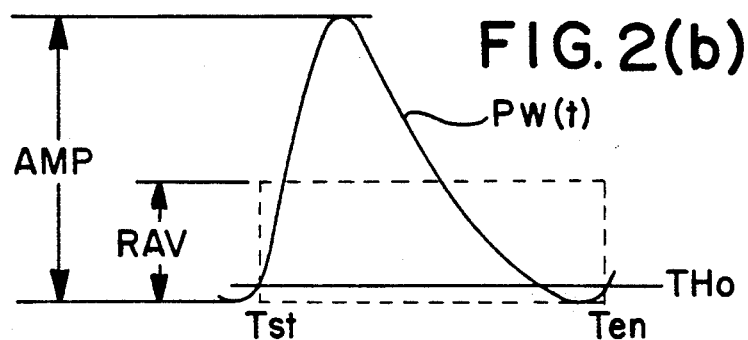

Thereafter, the integrated level RAV (%) which is given as the time average of the pulse wave Pw(t) normalized by the amplitude AMP is computed according to the following equation (1) (ST 103, refer to FIG. 2(b)).

$$RAV = \frac{\sum_{t=Tst}^{Ten} Pw(t)}{AMP(Ten - Tst)} \times 100 \qquad (1)$$

Figure 2C:
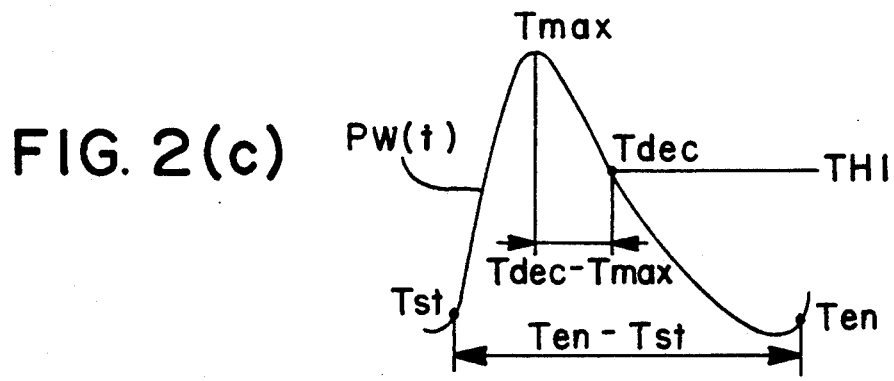
Figure 2D:
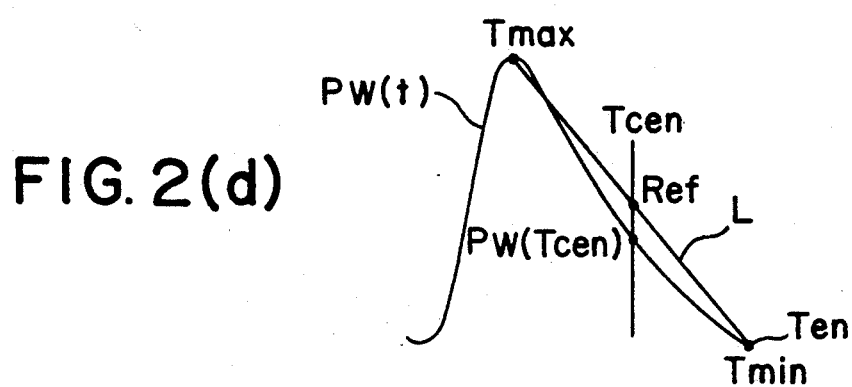

Then, the wave width ratio WID (%) is computed (ST 104 through ST 108, refer to FIG. 2(c)). WID is given by normalizing, with the period of the pulse wave (Ten−Tst), the time interval from the time point at which the pulse wave Pw(t) takes the maximum value Pwmax until it diminishes to a predetermined threshold level TH1.

First of all, the threshold level TH1 is determined according to the following equation (2) in which x is a constant predetermined in the range between 0 and 1 (ST 104).

$$TH1 = Pwmin + AMP \, X + \qquad (2)$$

Then, the time t is set at Tmax (ST 105) and a sampling interval t is added to t (ST 106) until the level of the pulse amplitude falls below TH1 (ST 107). If the determination result of ST 107 is NO, the system flow branches off to ST 106. If the determination result of ST 107 is YES, the system flow branches off to ST 108. In ST 108, WID is computed according to the following equation (3):

$$WID = \frac{Tdec - Tmax}{Ten - Tst} \times 100 \qquad (3)$$

where Tdec is the time point at which Pw(t) ≦ TH1.

Finally, the degree of curving CON (%) is computed (ST 109 through 111). CON is a relative ratio of the level of a reference line L connecting a maximum point and a minimum point of the pulse wave to the pulse wave Pw(t) at a point Tcen given as a point dividing the time interval (Tmax, Tmin) between the points of maximum and minimum values within a single cycle of the pulse to a predetermined ratio y.

Tcen is obtained according to the following equation (4) (ST 109) where y is a predetermined constant.

$$Tcen = Tmax + (Ten - Tmax) \, X \, y \qquad (4)$$

Then, the level Ref of the reference line L is computed according to the following equation (5) (ST 110).

$$Ref = Pwmax - AMP \, X \, y \qquad (5)$$

Thereafter, CON is computed according to the following equation (6).

$$CON = \frac{Pw(Tcen) - Pwmin}{Ref - Pwmin} \times 100 \qquad (6)$$

Figure 8:
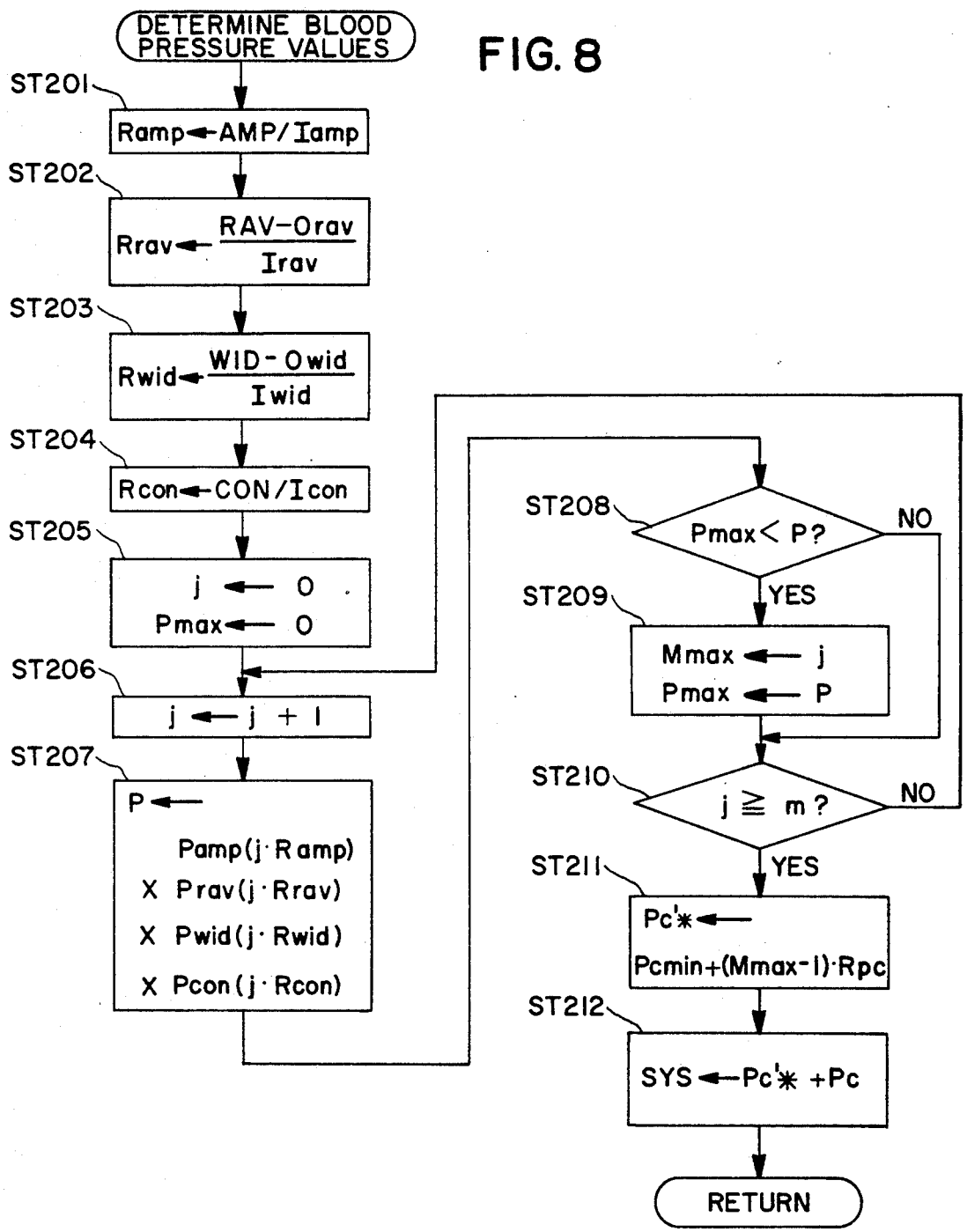
FIG. 8 is a flow chart describing the process of determining blood pressure values in the electronic blood pressure meter.
Figure 9A:
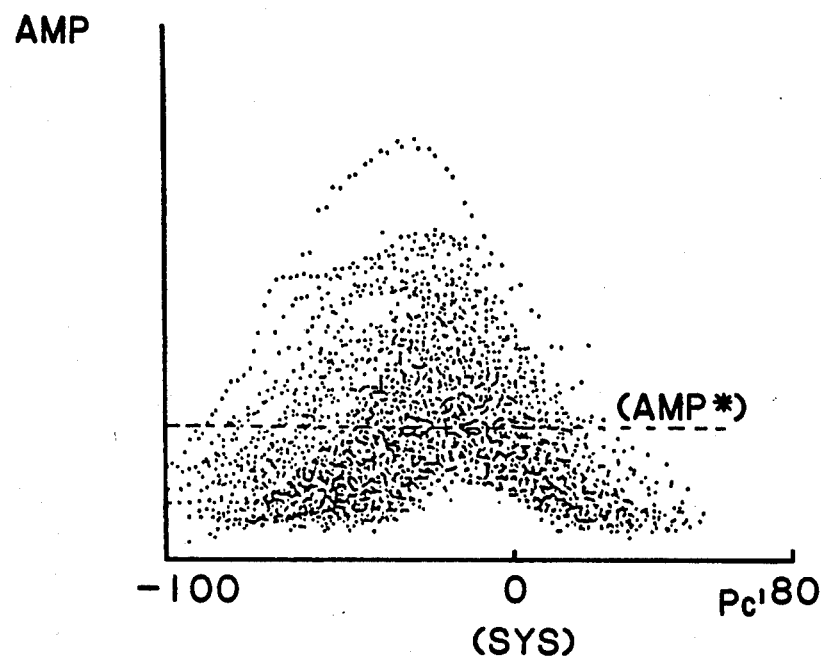
FIGS. 9(a), 9(b), 9(c) and 9(d) are graphs of actually measured data for showing the relationship between the relative cuff pressure and the pulse wave amplitude, the integrated level, the pulse wave width ratio and the degree of curving, respectively.
Figure 9B:
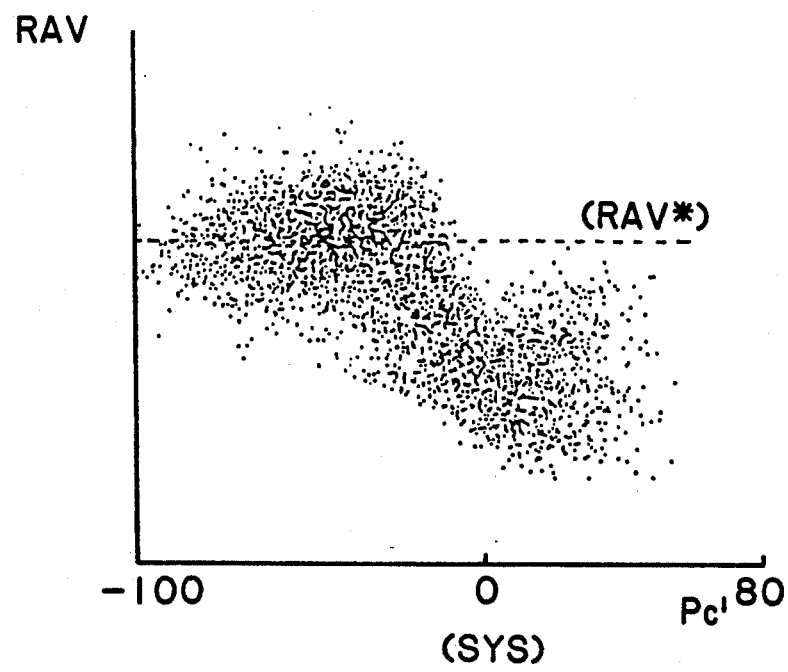
Figure 9C:
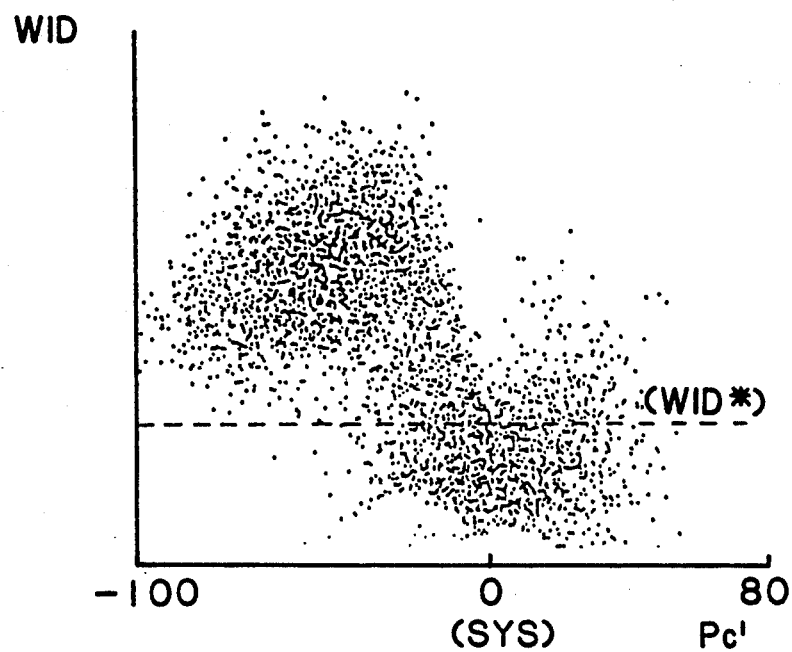
Figure 9D:
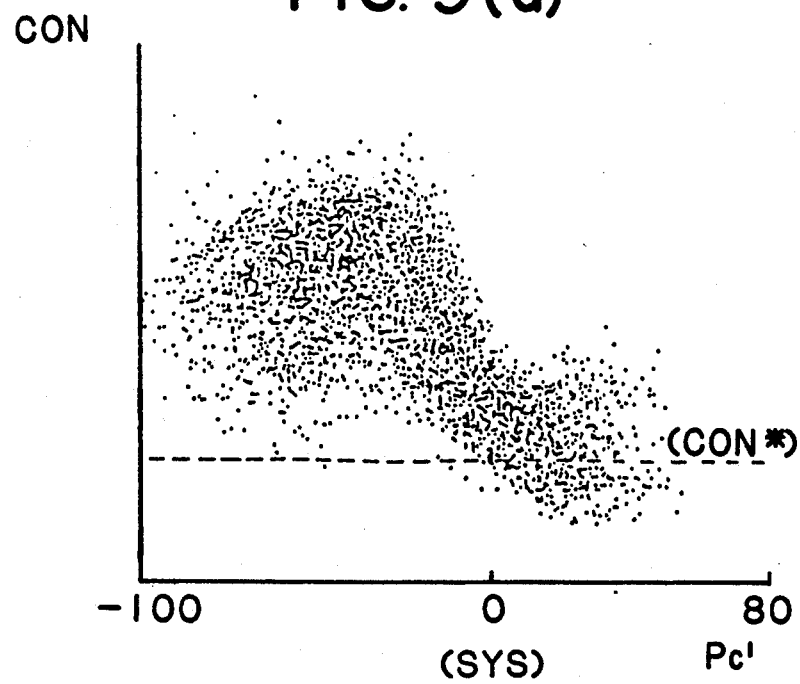

Now the process of determining the blood pressure values is described in the following with reference to FIGS. 1, 8 and 9.

In ST 201 through 204, the parameters AMP, RAV, WID and CON are classified into ranks. Since the data table of the membership functions which are referred to hereinafter is discrete, it is necessary to carry out a corresponding ranking process which is, in more specific terms, carried out according to the following equations (7) through (10):

$$Ramp = AMP/Iamp \quad (7)$$

$$Rrav = (RAV - Orav)/Irav \quad (8)$$

$$Rwid = (WID - Owid)/Iwid \quad (9)$$

$$Rcon = CON/Icon \quad (10)$$

where Iamp, Irav, Iwid and Icon are rank widths, and Orav and Owid are offset values. Since the minimum values of RAV and WID are not zero, they are divided by their rank widths Irav and Iwid, respectively, after subtracting their offset values Orav and Owid, respectively, therefrom.

In the steps following ST 205, blood pressure values are computed by using the parameters Ramp, Rrav, Rwid and Rcon which are classified into ranks as mentioned above. Now, before describing the specific process thereof, the data table is described in the following.

FIGS. 9(a) through 9(d) show graphs obtained by plotting the actually measured data of AMP, RAV, WID and CON obtained from a large number of subject persons with the relative pressure Pc' taken along the horizontal axis. Each of these graphs represents a probability density distribution using the associated parameter and the relative pressure as its variables, and these graphs are used as membership functions. Now, in FIGS. 9(a) through 9(d), suppose the parameters are AMP*, RAV*, WID* and CON*. The cut sections of these membership functions obtained by cutting them with AMP*, RAV*, WID* and CON* are given as shown in FIGS. 1(a) through 1(d). Thus, FIGS. 9(a) through 9(d) can be considered as membership functions which are selected for AMP*, RAV*, WID* and CON*, respectively.

According to the electronic blood pressure meter of the present invention, the parameters and the relative cuff pressure Pc' are classified into ranks, and the membership functions are stored in the memory 10a in the form of a discrete data table. For instance, if Pc' and AMP are classified into m and n ranks, respectively, the membership functions for AMP can then be expressed by the following matrix:

$$\begin{bmatrix} Pamp(1,1), & ---, & Pamp(1,n) \\ Pamp(2,1), & ---, & Pamp(2,n) \\ - & - & - \\ Pamp(m,1), & ---, & Pamp(m,n) \end{bmatrix}$$

If AMP is computed, and its classified value is Ramp, the vertical column containing Ramp is selected as the membership function corresponding to this value of AMP.

Returning now to the description of the process in ST 205, the initial values of the pointer j of the relative cuff pressure Pc' and the variable Pmax storing the maximum value of the multiplied membership function are set to zero. j is incremented in ST 206, and a multiplication process is carried out on the membership function in ST 207 according to the following equation (11):

$$P = Pamp(j,Ramp) \times Prav(j,Rrav) \times Pwid(j,Rwid) \times Pcon(j,Rcon) \quad (11)$$

In ST 208, it is determined whether P computed in ST is larger than Pmax or not. The program flow branches off to ST 210 if this determination result is YES, and to ST 209 if this determination result is NO. In ST 209, j and p are substituted into Mmax and Pmax. It is then determined if j is less than m or not in ST 210. The program flow then branches off to ST 206 if this determination result is NO, and to ST 211 if this determination result is YES.

The processes in ST 206 through 210 are repeated until the determination result of ST 210 becomes YES, and these processes correspond to the process of computing a function P which is obtained by multiplying the membership functions corresponding to the parameters AMP, RAV, WID and CON, and extracting its maximum value Pmax as indicated in FIG. 1.

In ST 211, the relative cuff pressure Pc'* can be estimated from the obtained Mmax and Pmax according to the following equation (12):

$$Pc'^* = Pcmin + (Mmax - 1) \times Rpc \quad (12)$$

where Rpc is the rank width of the relative cuff pressure Pc'.

In ST 212, the systolic blood pressure is obtained by adding the current cuff pressure Pc to the estimated relative cuff pressure Pc'*:

$$SYS = Pc'^* + Pc \quad (13)$$

A multiplication was used for estimating the relative cuff pressure Pc' according to this embodiment, but it is also possible to use addition and other logical operations as a design choice.

Thus, according to the first embodiment of the present invention, the time interval required for blood pressure measurement can be reduced as a measurement process can be completed in a single cycle of pulse wave.

Now a second embodiment of the electronic blood pressure meter of the present invention is described in the following with reference to FIGS. 10 and 11. The hardware structure of this electronic blood pressure meter is substantially identical to the one shown in FIG. 5, and the second embodiment is characterized by its operation in regard to the determination of the sufficiency of initial cuff pressurization.

Figure 10:
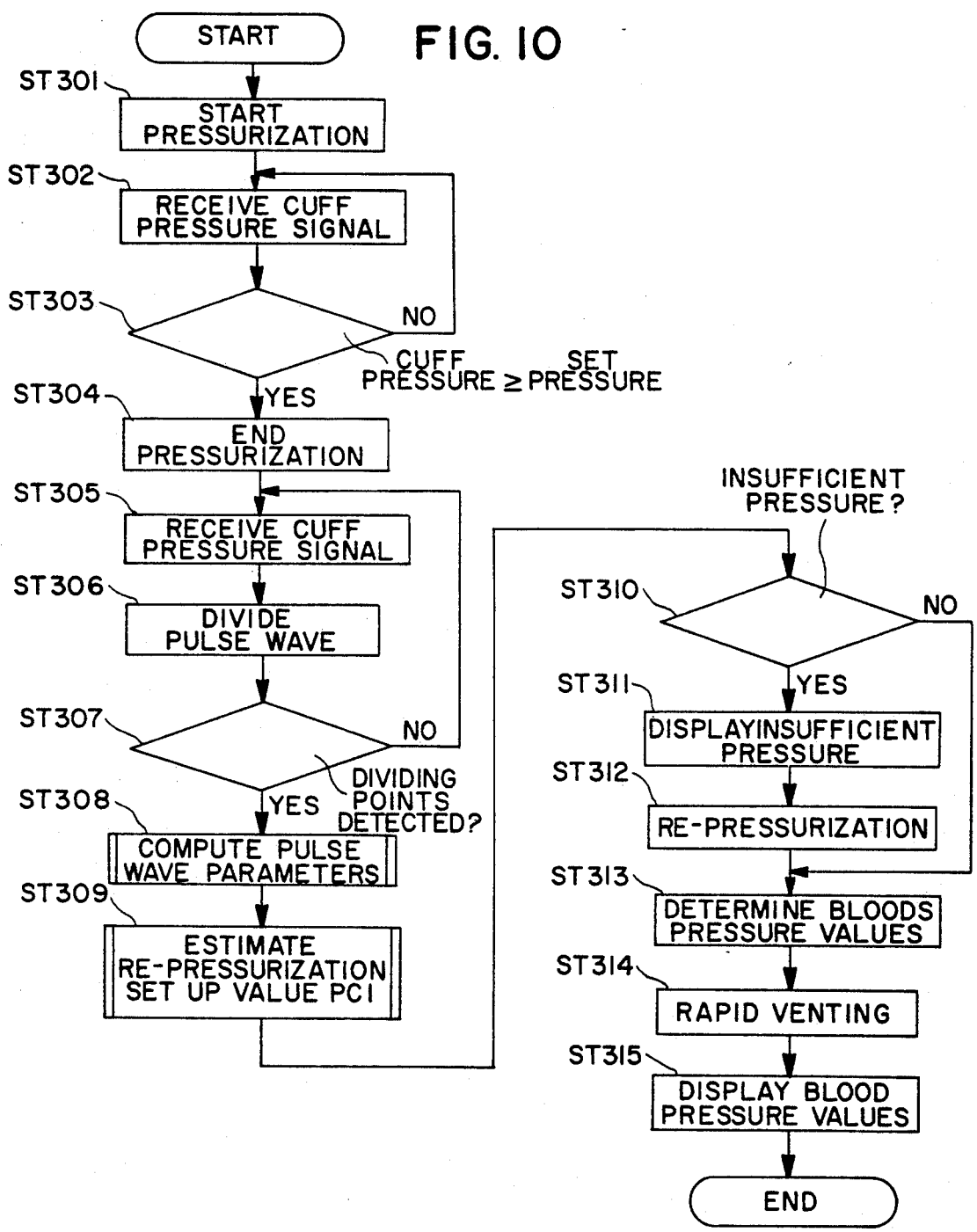
FIG. 10 is a flow chart showing the overall operation of a second embodiment of the electronic blood pressure meter according to the present invention.

Referring to FIG. 10, according to this second embodiment of the electronic blood pressure meter, first of all, the cuff 2 is wrapped around an upper arm of a subject person, and a process of blood pressure measurement is started. The pressurization pump 4 is turned on with the vent valve 3 closed to start the process of pressurization (ST 301). The MPU 10 receives the cuff pressure signal from the A/D converter 8 (ST 302), and determines if the current cuff pressure has reached a predetermined set pressure value PcO (ST 303). If the result of this determination process is NO, the system flow branches off to ST 302. If the result is YES, the program flow branches off to ST 304. In other words, the processes in ST 302 and ST 303 are repeated until the current cuff pressure reaches the set pressure value PcO. This set pressure value PcO may be either fixed or variable by providing a set up switch which may be freely adjusted by the user of the electronic blood pressure meter.

In ST 304, the MPU 10 stops the pressurization pump 4. The MPU 10 then receives pulse wave Pw(t), and slices the pulse wave by applying a threshold value THO to this pulse wave Pw(t) (refer to FIG. 2(b)). The MPU 10 then determines if dividing points Tst and Ten have been detected from the pulse wave Pw(t) (ST 307), and if the determination result is NO the system flow branches off to ST 305. Otherwise, the system flow branches off to ST 308. In other words, the processes in ST 305 through ST 307 are repeated until one cycle of pulse wave is obtained.

In ST 308, the MPU 10 computes four parameters which were described previously from the pulse wave Pw(t). The parameters are computed after detecting a full cycle of pulse wave according to this embodiment, but an even higher reliability can be obtained by detecting a number of cycles of pulse wave and taking average values of parameter values obtained from different cycles of the pulse wave.

In ST 309, the MPU 10 estimates a repressurization set up value Pc1 from the parameters obtained in ST 308. In ST 310, a comparison is made between this re-pressurization set up value Pc1 and the initial set pressure value PcO: pressurization insufficiency is detected and the system flow branches off to ST 311 if the re-pressurization set up value Pc1< is larger than the initial set pressure value PcO (Pc1 PcO), and no insufficiency is detected and the system flow branches off to ST 313 if Pc1 is less than PcO (Pc1≦PcO).

In ST 311, the MPU 10 indicates insufficiency of pressurization on the display unit 9. It is also possible to notify insufficiency of pressurization by sound in addition to the visual display.

In ST S12, the MPU 10 again activates the pressurization pump 4, and carries out a repressurization process until the re-pressurization set up value Pc1 is reached. In ST 313, the MPU 10 determines blood pressure values according to the oscillometric method. During this blood pressure value determining process, the vent valve 3 is placed under a gradual venting mode, and the pulse wave amplitude is detected during this gradual venting process. The pulse wave amplitude increases as the cuff pressure diminishes, and reaches a peak value when the cuff pressure reaches a level approximately equal to the average value of the systolic blood pressure and the diastolic blood pressure before the pulse wave amplitude starts diminishing. The cuff pressure corresponds to the systolic blood pressure when the pulse wave amplitude during its increasing phase corresponds to about 50% of its maximum amplitude, and the cuff pressure corresponds to the diastolic blood pressure when the pulse wave amplitude during its decreasing phase corresponds to about 70% of the diastolic blood pressure. It is thus possible to determine the blood pressure values according to this information. Since the second embodiment of the does not depend on the mode of determining blood pressure values, no further detailed description thereof is given here. The process of determining blood pressure values may be freely selected as a design choice, and may also be based on the Korotkoff method.

In ST 314, the MPU 10 brings the vent valve 3 into a rapid venting mode, and relieves the upper arm of the subject person from pressure by rapidly venting the cuff 2. The MPU 10 also displays the determined blood pressure values on the display unit 9 (ST 315).

The process of computing the pulse wave parameters (ST 308) is carried out substantially in the same way as that for the first embodiment which was described with reference to FIG. 7.

Now the process of estimating the repressurization set up value is described in the following with reference to FIGS. 1, 9 and 11.

In ST 401 through 404, the parameters AMP, RAV, WID and CON are classified into ranks. Since the data table of the membership functions which are referred to hereinafter is discrete, it is necessary to carry out a corresponding ranking process which is, in more specific terms, carried out according to the following equations (7) through (10) in the same way as in the previous embodiment:

$$Ramp = AMP/Iamp \qquad (7)$$

$$Rrav = (RAV - Orav)/Irav \qquad (8)$$

$$Rwid = (WID - Owid)/Iwid \qquad (9)$$

$$Rcon = CON/Icon \qquad (10)$$

In the steps following ST 405, the repressurization set up value is estimated by using the parameters Ramp, Rrav, Rwid and Rcon which are classified into ranks as mentioned above. Now, before describing the specific process thereof, the data table is described in the following.

FIGS. 9(a) through 9(d) show graphs obtained by plotting the actually measured data of AMP, RAV, WID and CON obtained from a large number of subject persons with the relative pressure Pc' taken along the horizontal axis. Each of these graphs represents a probability density distribution using the associated parameter and the relative pressure as its variables, and these graphs are used as membership functions. Now, in FIGS. 9(a) through 9(d), suppose the parameters are AMP*, RAV*, WID* and CON*. The cut sections of these membership functions obtained by cutting them with AMP*, RAV*, WID* and CON* are given as shown in FIGS. 1(a) through 1(d). Thus, FIGS. 9(a) through 9(d) can be considered as membership functions which are selected for AMP*, RAV*, WID* and CON*, respectively.

According to this embodiment of the electronic blood pressure meter according to the present invention, the parameters and the relative cuff pressure Pc' are classified into ranks, and the membership functions are stored in the memory 10a in the form of a discrete data table. For instance, if Pc' and AMP are classified into m and n ranks, respectively, the membership functions for AMP can then be expressed by the following matrix:

$$\begin{bmatrix} Pamp(1,1), & \cdots, & Pamp(1,n) \\ Pamp(2,1), & \cdots, & Pamp(2,n) \\ \vdots & & \\ Pamp(m,1), & \cdots, & Pamp(m,n) \end{bmatrix}$$

If AMP is computed, and its classified value is Ramp, the vertical column containing Ramp is selected as the membership function corresponding to this value of AMP.

Returning now to the description of the process in ST 405, the initial values of the pointer j of the relative cuff pressure Pc' and the variable Pmax storing the maximum value of the multiplied membership function are set to zero. j is incremented in ST 406, and a multiplication process is carried out on the membership function in ST 407 according to the following equation (11):

$$P = Pamp(j, Ramp) \times Prav(j, Rrav) \times Pwid(j, Rwid) \times Pcon(j, Rcon) \qquad (11)$$

In ST 408, it is determined whether P computed in ST 407 is larger than Pmax or not. The program flow branches off to ST 410 if this determination result is YES, and to ST 409 if this determination result is NO. In ST 409, j and P are substituted into Mmax and Pmax. It is then determined if j is less than m or not in ST 410. The program flow then branches off to ST 406 if this determination result is NO, and to ST 411 if this determination result is YES.

The processes in ST 406 through 410 are repeated until the determination result of ST 410 becomes YES, and these processes correspond to the process of computing a function P which is obtained by multiplying the membership functions corresponding to the parameters AMP, RAV, WID and CON, and extracting its maximum value Pmax as indicated in FIG. 1.

In ST 411, the relative cuff pressure Pc'* can be estimated from the obtained Mmax and Pmax according to the following equation (12):

$$Pc'^* = Pcmin + (Mmax - 1) \times Rpc \qquad (12)$$

In ST 412, the estimated relative cuff pressure Pc' is subtracted from the initial set pressure value Pc0 to estimate the re-pressurization set up value Pc1. If the relative cuff pressure Pc' is positive, the set pressure value Pc0 is higher than the systolic blood pressure, and the re-pressurization set up value Pc1 is less than Pc0 with the result that the determination result of ST 10 becomes NO. Conversely, if the relative cuff pressure Pc' is negative, the set pressure value Pc0 is less than the systolic blood pressure and the re-pressurization set up value Pc1 is higher than PC0 with the result that the determination result of ST 10 becomes YES.

The re-pressurization was to be carried out automatically in the above described embodiment, but it is also possible to display the amount of re-pressurization (difference between the re-pressurization set up value and the initial set pressure value) along with the fact of insufficiency in re-pressurization so that the user may carry out the re-pressurization according to the display.

Thus, according to the second embodiment of the present invention, it is possible not only to accurately determine insufficiency of pressurization after completion of the process of initial pressurization but also to know the amount of insufficiency so that only one process of re-pressurization would be sufficient. Therefore, no great care is necessary in determining the initial set pressure value, and the user can avoid setting an unnecessarily high initial set pressure value. Also, since the insufficiency of re-pressurization is detected from pulse wave, errors in detecting insufficiency in pressurization due to external noises can be avoided, and the risk of inflicting undue pain and blockage of blood flow can be reduced. The elimination of the need for repeated re-pressurization can contribute to the improvement in the efficiency of measurement.

Now a third embodiment of the electronic blood pressure meter of the present invention given here as a continuous blood pressure monitoring device is described in the following with reference to FIGS. 12 through 22. The hardware structure of this continuous blood pressure monitoring device is similar to the one shown in FIG. 5, and the third embodiment is characterized by its operation which is programmed in its MPU 10.

The MPU 10 is provided with the function to determine blood pressure values from the amplitude of the pulse wave obtained during the process of gradual depressurization (normal measurement), the function to compute pulse wave parameters, the function to store the relationship (which is referred to simply as characteristic function hereinafter) between the pulse wave parameters obtained by the normal measurement process and the relative pressure (the difference between the cuff pressure and the blood pressure values determined by the normal measurement process) in the memory 10a, the function to compute membership functions according to the pulse wave parameters as a result of a short time measurement process which is described hereinafter and the characteristic functions, and the function to determine blood pressure values from the membership functions.

The MPU 10 is connected to a display unit 9 for displaying determined blood pressure values. It is also possible to connect a printer to this device to print out blood pressure values although it is not shown in the drawings.

Figure 18:
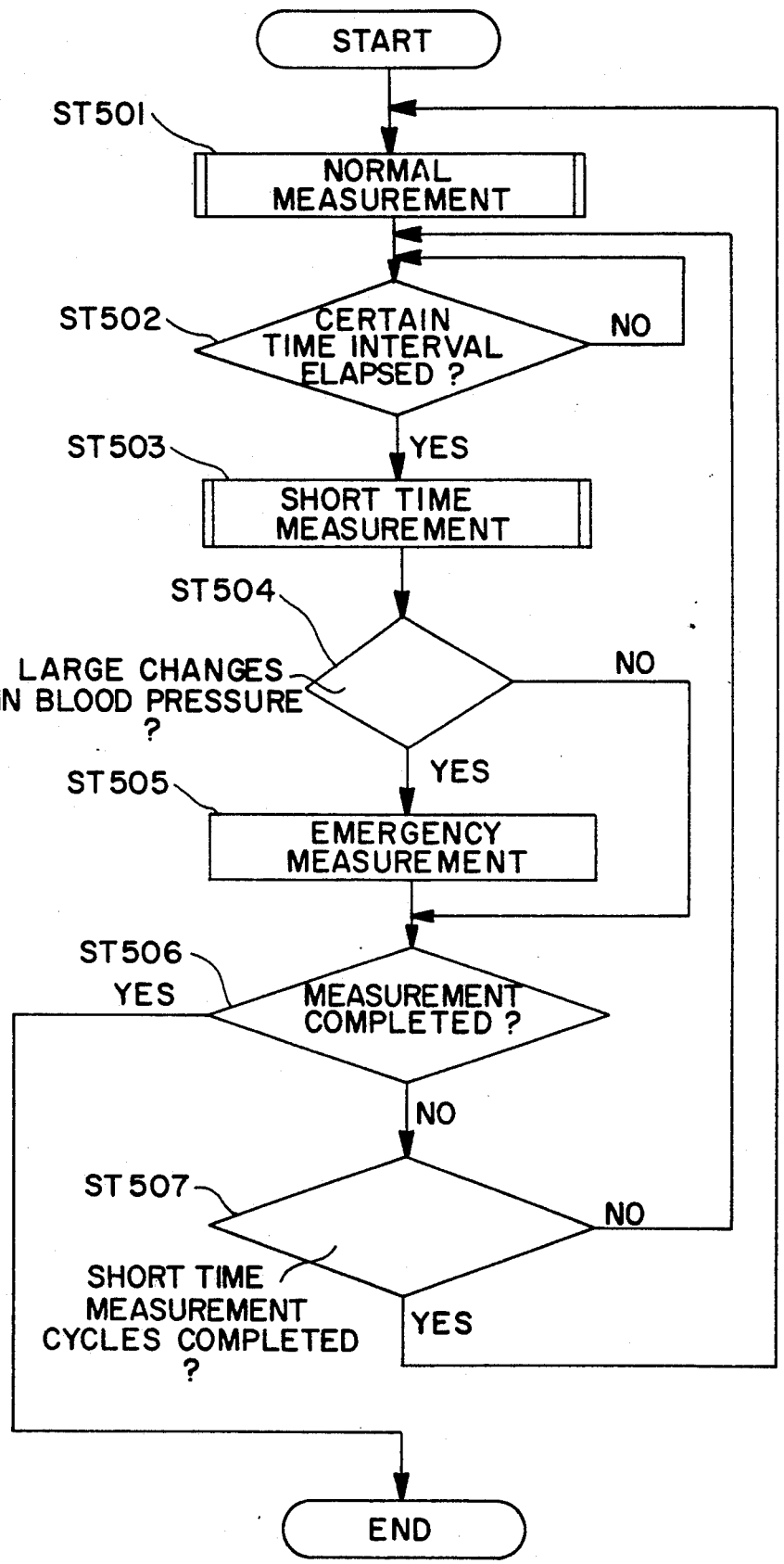
FIG. 18 is a flow chart showing the overall operation of the continuous blood pressure monitoring device.

Now the overall operation of the continuous blood pressure monitoring device of this embodiment is described in the following with reference to FIG. 18.

First of all, a normal measurement process is carried out (ST 501). In this normal measurement process, after the cuff is rapidly pressurized to a predetermined initial pressure, blood pressure values are determined according to the amplitude of the pulse wave (which also serves as one of the pulse wave parameters) obtained during the gradual depressurization of the cuff 2, and, in the meantime, the pulse wave parameters are computed and stored in the memory 10a in associated with the relative pressure.

In ST 502, it is determined whether a certain time period (measurement interval) has elapsed after completion of a normal measurement process. The program flow stays at ST 502 as long as the determination result is NO, but branches off to ST 503 when the determination result has changed to YES.

In ST 503, a short time measurement is carried out. In this short time measurement, after the cuff is pressurized to a predetermined pressure value, blood pressure values are determined by detecting a few cycles of pulse wave.

In ST 504, the program flow branches off to ST 505 if the blood pressure values obtained by the short time measurement are much different from the previously obtained values or higher or lower than a predetermined limit value, and otherwise branches off to ST 506. In ST 505, an emergency measurement is carried out. The emergency measurement is the same as the normal measurement. The initial pressure is set as low a level as possible according to the systolic blood pressure obtained by the previous short time measurement so that blood pressure values may be obtained as soon as possible.

In ST 506, it is determined if the measurement is completed or not. When the determination result is YES, the measurement is concluded. If the determination result is NO, the system flow branches off to ST 507. In ST 507, it is determined if the short time measurement has been conducted for a predetermined number of times. The program flow branches off to ST 501 if the determination result is YES and to ST 502 if the determination result is NO. In other words, the normal measurement is carried out once for a predetermined number of times of short time measurement, and the 5 characteristic functions are updated.

Figure 16:
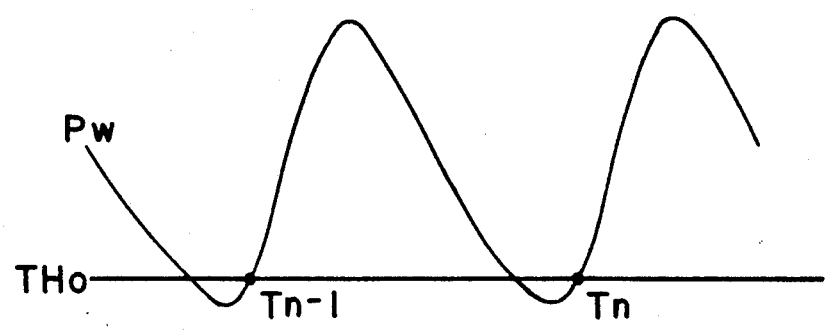
FIG. 16 is a waveform diagram showing the process of dividing the pulse wave in the continuous blood pressure monitoring device.
Figure 17:
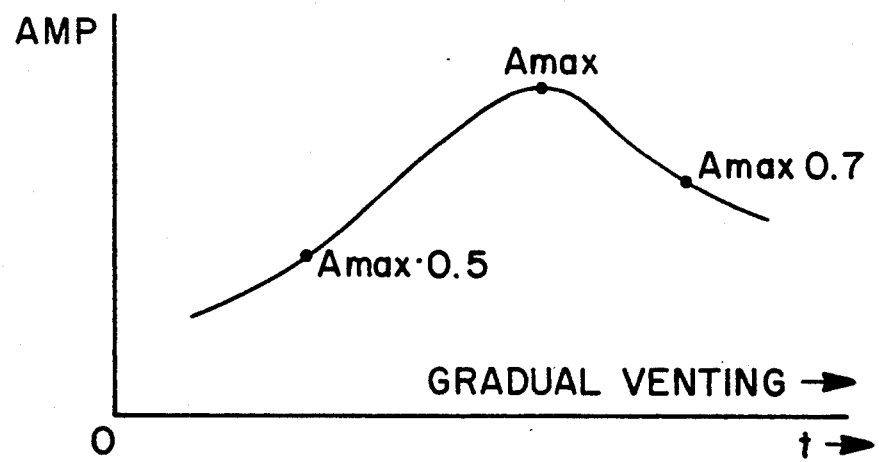
FIG. 17 is a graph showing the process of determining blood pressure values during the process of normal measurement in the continuous blood pressure monitoring device.
Figure 19:
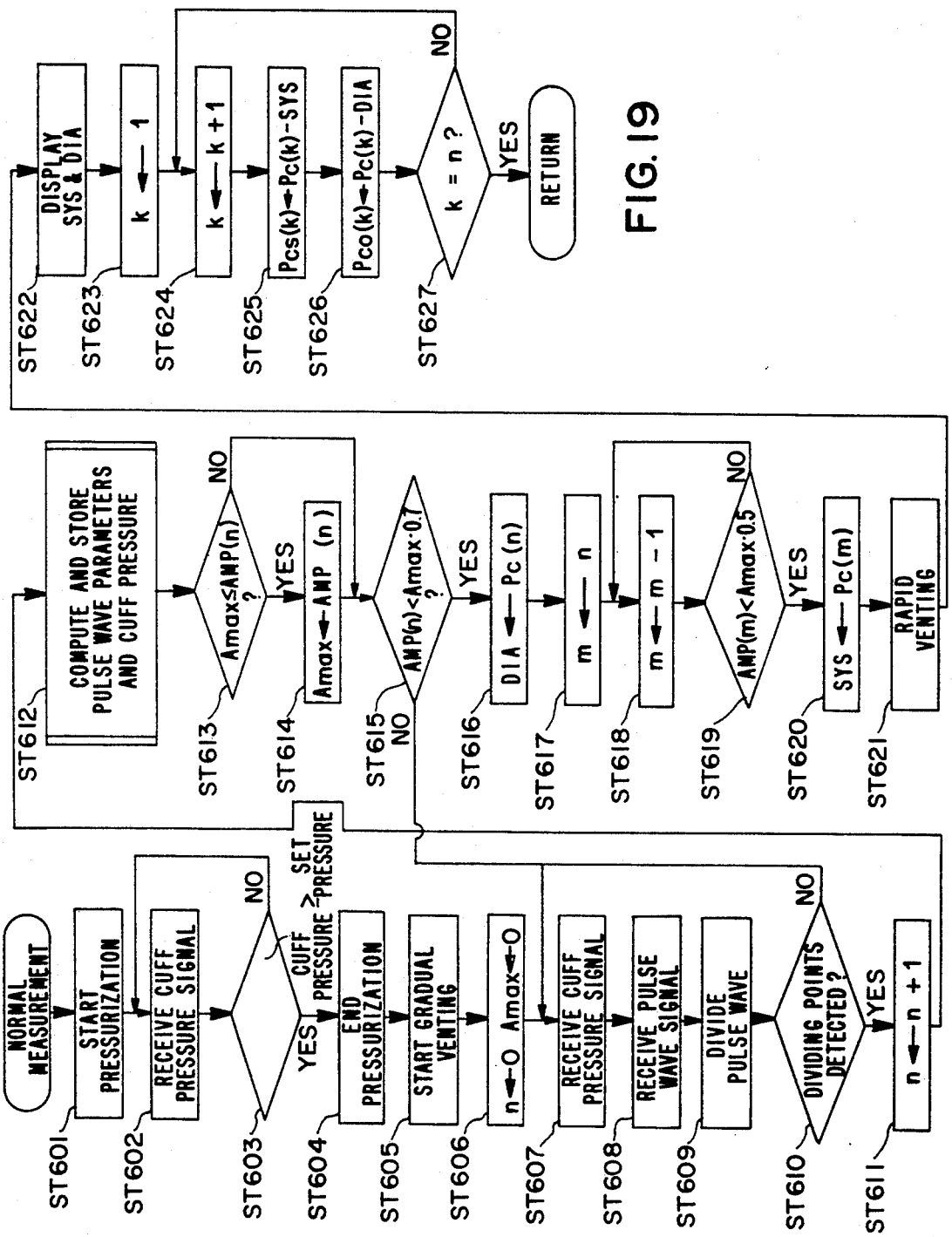
FIG. 19 is a flow chart describing the process of normal measurement in the continuous blood pressure monitoring device.

Now the details of the above mentioned process of normal measurement are described in the following with reference to FIGS. 16, 17 and 19.

First of all, the outline of the process of determining blood pressure values during the normal measurement process is described with reference to FIG. 17. The pulse wave amplitude AMP increases as the cuff pressure is gradually reduce, and after reaching a peak value of Amax starts diminishing again. The cuff pressure Pc is determined as the systolic blood pressure SYS when the pulse wave amplitude during its increasing phase corresponds to about 50% of Amax, and the cuff pressure Pc is determined as the diastolic blood pressure DIA when the pulse wave amplitude during its decreasing phase corresponds to about 70% of Amax. It is thus possible to determine the blood pressure values according to this information. Of course, the method for the normal measurement is not limited by this process. It is also possible to use the Korotkoff sound to determine blood pressure values and in this case also it is necessary to detect the pulse wave, and to compute and store pulse wave parameters. Now, the details of the process are described in the following.

Figure 11:
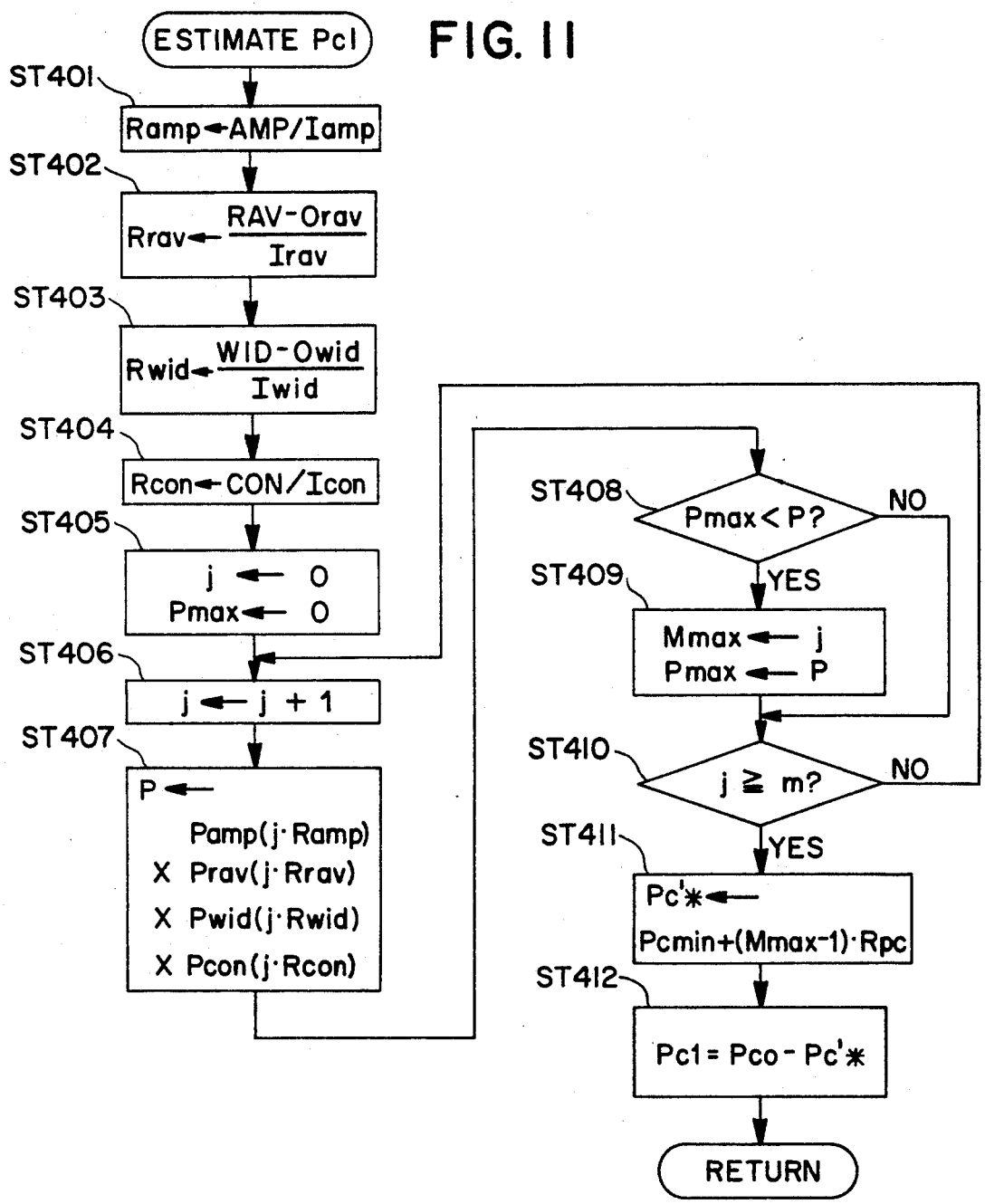
FIG. 11 is a flow chart describing the process of estimating the re-pressurization set up value in the second embodiment of the electronic blood pressure meter according to the present invention.
Figure 13A:
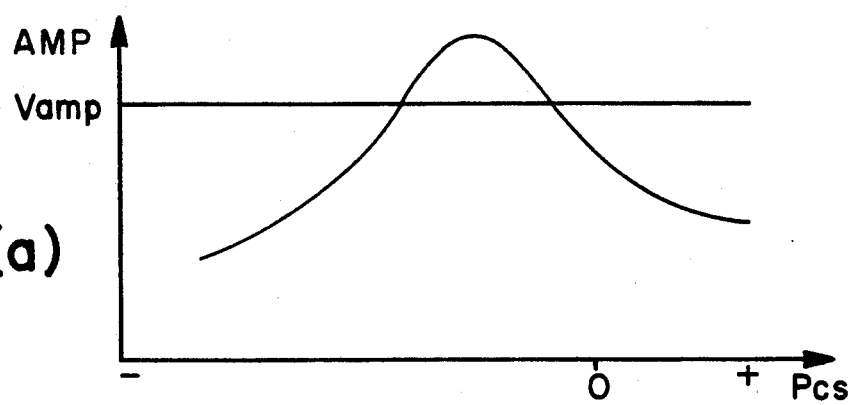
FIGS. 13(a) through 13(d) are graphs showing examples of characteristic functions of the pulse wave parameters for a continuous blood pressure monitoring device given here as a third embodiment of the present invention.
Figure 13B:
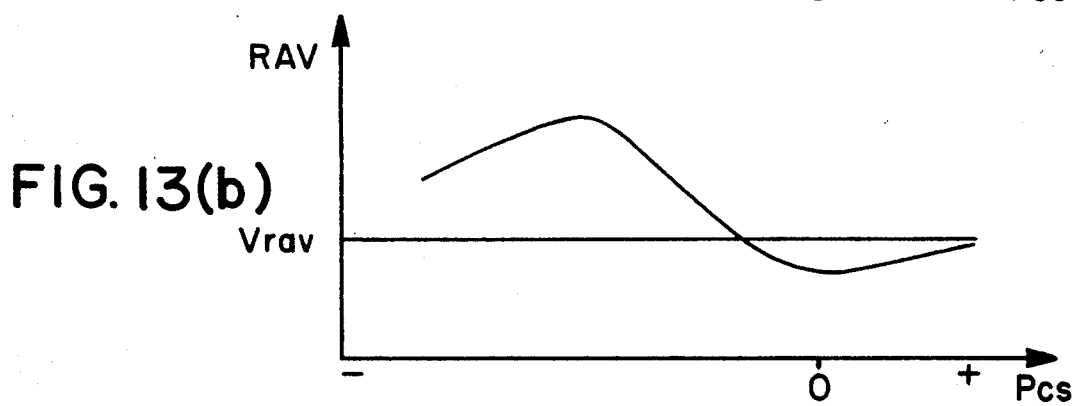
Figure 13C:
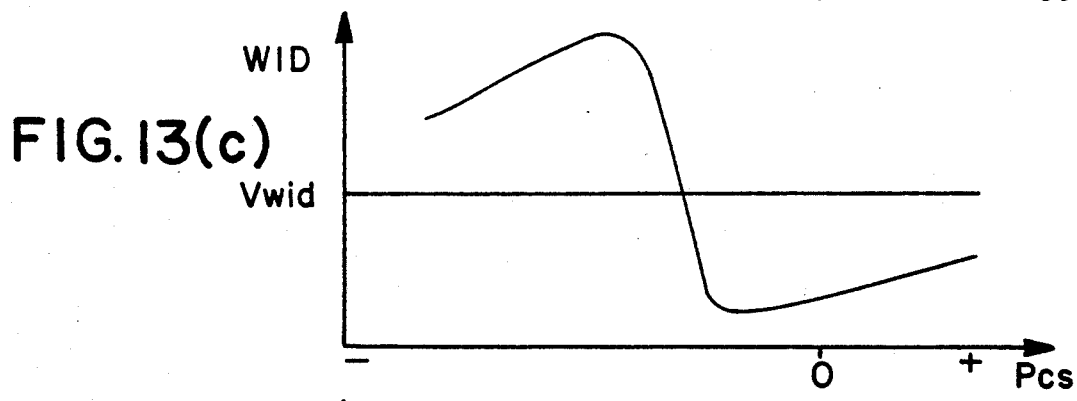
Figure 13D:
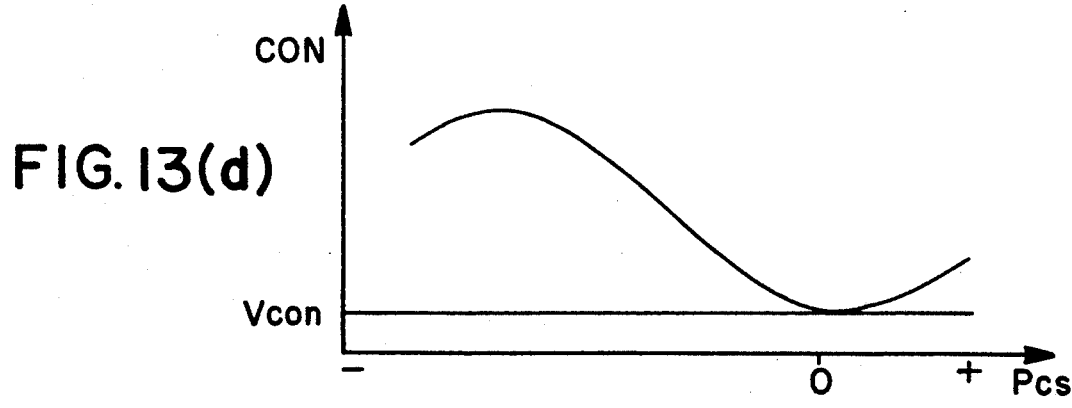

First of all, the MPU 10 closes the vent valve 3 and starts activating the pressurization pump 4 (ST 601, refer to FIG. 11). The MPU 10 then receives the cuff pressure signal from the A/D converter 8 (ST 602), and it is determined if the cuff pressure has reached a predetermined initial pressure level (ST 603). The program flow branches off to ST 602 if the determination result is NO and to ST 604 if the determination result is YES. This initial pressure level is required to be slightly higher than the systolic blood pressure of the patient, and is required to be predetermined.

In ST 604, the MPU 10 starts the pressurization pump 4, and sets the vent valve 3 into a gradual venting mode (ST 605). At the same time the counter n and the pulse wave amplitude maximum value Amax are both set to zero (ST 606).

In ST 607, the MPU 10 receives the cuff signal and the pulse wave signal (ST 608). The MPU 10 applies a threshold value THO to the pulse wave signal Pw to divide the pulse wave signal Pw into each cycle (ST 609, refer to FIG. 16). The MPU 10 then determines if a dividing point Tn has been detected or not, and if the determination result is NO the program flow branches off to ST 607 to continue the process of detecting the cuff pressure and the pulse wave.

If the determination result of ST 610 is YES, the program flow branches off to ST 611 and n is incremented. In ST 612, the pulse wave parameters (amplitude AMP, integration level RAV, pulse wave width ratio WID and degree of curving CON) for the n-th pulse wave, and the average value Pc(n) of the cuff pressure are computed and stored in the memory 10a. The process of computing the pulse wave parameters is described hereinafter in more detail).

In ST 613, the MPU 10 determines the amplitude AMP(n) for the n-th pulse wave is larger than Amax or not. The program flow branches off to ST 615 if the determination result is NO and to ST 614 if the determination result is YES. In ST 614, AMP(n) is set as the new value for Amax. In ST 615, it is determined if AMP(n) is less than 70% of Amax or not. If the determination result is NO, the program flow branches off to ST 607 to detect the next value of the pulse wave. If the determination result is YES, the program flow branches off to ST 616 to determine blood pressure values.

In ST 616, the MPU 10 determines the cuff pressure Pc(n) corresponding to the pulse wave when the determination result of ST 615 has become YES as the diastolic blood pressure DIA. In ST 617, the value of n at this point is substituted into the counter m. In ST 618, m is decremented, and it is determined if AMP(m) is smaller than 50% of Amax or not. If the determination result is NO, the program flow branches off to ST 618 to continue the process of searching.

If the determination result of ST 619 is YES, the program flow branches off to ST 620, and the cuff pressure PC(m) corresponding to m is set as the systolic blood pressure SYS. In ST 621, the MPU 10 sets the vent valve 3 into a rapid vent mode, and relieves the upper arm of the patient from pressure. In ST 622, the MPU 10 displays SYS and DIA on the display unit 9.

The process of ST 623 and the steps following them consist of computing the relative pressure values Pcs and Pcd. First of all, the counter k is set to 1 (ST 623) and after incrementing k (ST 624) the relative pressure value Pcs associated with the systolic blood pressure SYS is computed according to the following equation (14) (ST 625):

$$Pcs(k) = Pc(k) - SYS \qquad (14)$$

The relative pressure Pcd(k) associated with the diastolic blood pressure DIA is computed according to the following equation (15) (ST 626):

$$Pcd(k) = Pc(k) - DIA \qquad (15)$$

In ST 627, it is determined if k has become equal to n or not. The program flow branches off to ST 624 to continue the process if the determination result is NO, and concludes the process of normal measurement and returns to the main routine shown in FIG. 18 if the determination result is YES. Of course, obtained Pcs and Pcd are stored in the memory 10a.

Now the process of short time measurement is described in the following. The process of short time measurement makes use of pulse wave parameters which, for instance, may consist of the pulse wave parameters which were derived according to the process illustrated in FIGS. 2(a) through 2(d) and 7.

Now, referring to FIG. 20, first of all, the initial value of pressurization is set as the average value of the systolic blood pressure value and the diastolic blood pressure value ((SYS+DIA)/2) (ST 701). It suffices for the initial value of pressurization for short time measurement to be between the systolic blood pressure and the diastolic blood pressure, and is not required to be very precise.

Then, the cuff 2 is pressurized to this initial pressure level (ST 702). The process in ST 703 through 709 may be carried out either with the cuff pressure maintained at this initial pressure level or with the cuff pressure gradually reduced.

In ST 703 the counter i is set to zero, and in ST 704 the counter i is incremented. In ST 705, in the same way as in ST 609, the pulse wave is divided into each cycle, and the pulse wave parameters AMP, RAV, WID and CON are computed and stored in the memory 10a. The cuff pressure Pc at this time point is also stored in the memory 10a (ST 707).

In ST 708, it is determined whether i has reached a predetermined number or not. This predetermined number is so selected that a few cycles of pulse wave may be detected. It suffices to detect a single cycle of pulse wave in the short time measurement in theory, but as it may not be possible to obtain accurate pulse wave parameters due to the movement of the patient a few cycles of pulse wave are detected in the present embodiment to compute pulse wave parameters for each of these cycles, and take average values thereof.

In ST 709, the average values of the pulse wave parameters Vamp, Vrav, Vwid and Vcon and the average value Pc of the cuff pressure are computed, and are stored in the memory 10a before the vent valve 3 is put into the rapid vent mode to release the upper arm from pressure (ST 710).

In ST 711 data is applied to the pulse wave parameters to compute the membership functions, and in ST 712 the blood pressure values SYS and DIA are determined by carrying out a logical computation on these membership functions. The details of the process in ST 711 and 712 are described hereinafter.

Finally, the determined blood pressure values SYS and DIA are displayed on the display unit 9 (ST 713), and the short time measurement is concluded.

Now the processes of computing the membership functions of ST 711 and carrying out the logical computation of ST 712 are described in the following. The following description is directed to the systolic blood pressure, but can be equally applied to the diastolic blood pressure.

Figure 14A:
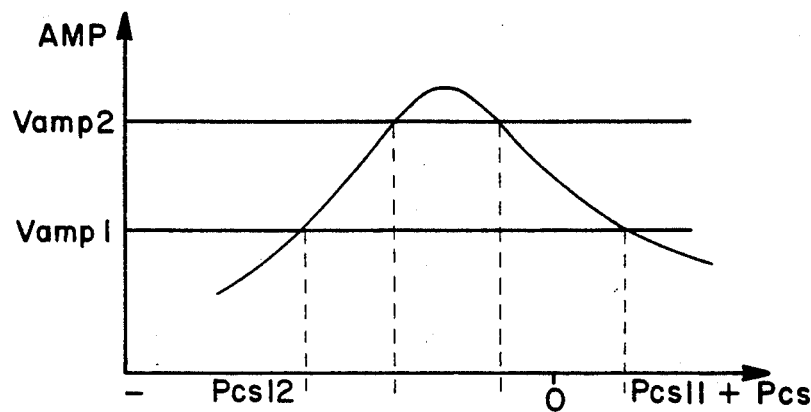
FIGS. 14(a) through 14(c) are diagrams showing the process of computing the membership functions from the characteristic functions for the pulse wave amplitude in the continuous blood pressure monitoring device.

First of all, the outline of the process of computing the membership functions is described with reference to FIGS. 14(a) through 14(c). FIG. 14(a) shows an example of the amplitude AMP characteristic function obtained by a normal measurement. Suppose that the amplitude of the pulse wave obtained at the cuff pressure Pc is Vamp1. Then, it is probable that this cuff pressure Pc is either higher than the systolic blood pressure SYS by Pcs11 or lower than the systolic blood pressure SYS by Pcs12.

Figure 14B:
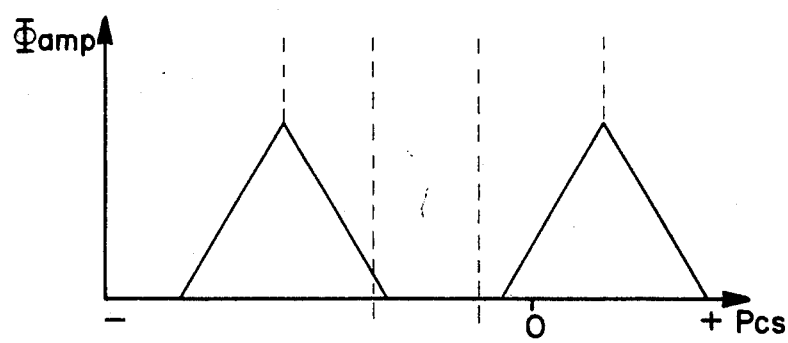
Figure 14C:
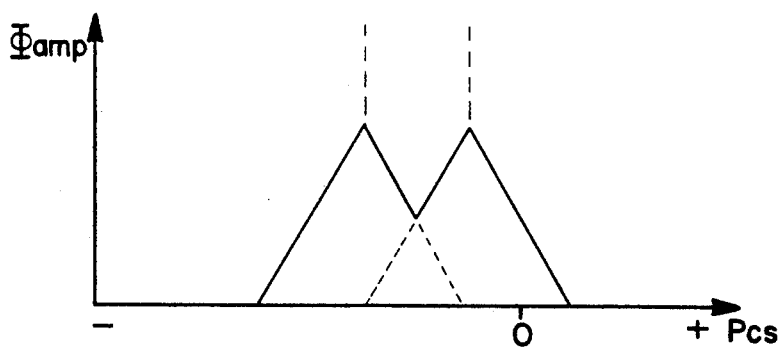

It is expressed by a membership function as given in FIG. 14(b). In this drawing, the horizontal axis represents the relative cuff pressure Pcs while the vertical axis represents the probability of the relative cuff pressure Pcs being at that value. According to this embodiment, the shape of the membership function is given as a triangle having a vertex (maximum point) located at the same point (intersection) as the pulse wave characteristic function Vamp, and a base having a certain width.

There may be a plurality of intersections, and there may be a same number of triangles as the number of the intersections. For instance, in the case of FIG. 14(b), there are two intersections, and, therefore, there are two triangles. And, these triangles may partly overlap each other as shown in FIG. 14(c), and the maximum values of these triangles are used as a membership function according to the present embodiment. Since the data stored in the memory 10a is discrete, the accuracy of the membership functions is increased by using linear interpolation.

The pulse wave amplitude was taken as an example in the above description, but the same principle holds with respect to the other parameters also. The maximum point of each membership function and the width of the base of each triangle may be determined by taking into account the weight carried by each of the parameters and the repeatability of each of the parameters. However, according to the present embodiment, each of the pulse wave parameters is treated in a uniform manner.

Now, referring to FIGS. 15(a), 15(b) and 21, the specific details of the process are described in the following. First of all, the point x is placed on the minimum value Pcsmin of the relative cuff pressure Pcs, and the count j is set to 1 (ST 801). The pointer x is incremented (ST 802), and it is determined if an intersection between the characteristic function AMP of the pulse wave amplitude and Vamp has been obtained (ST 803, FIG. 12(a)). If this determination result is NO, the program flow branches off to ST 802. If YES, the program flow branches off to ST 804.

Figure 15A:
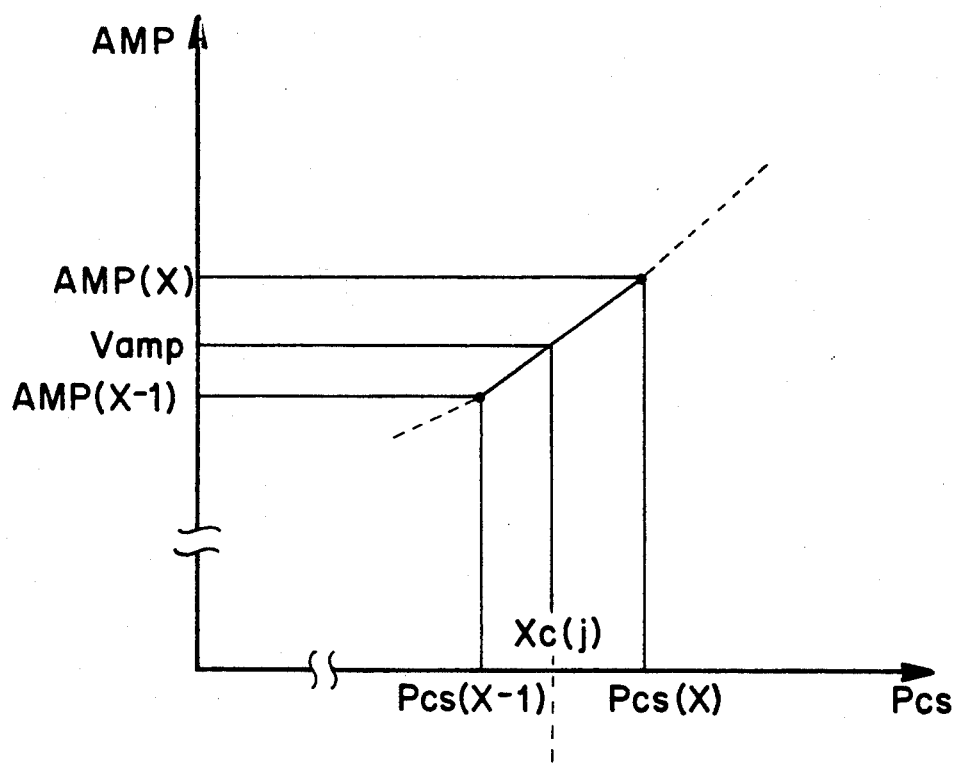
FIGS. 15(a) and 15(b) are diagrams showing the process of linear interpolation in computing one of the membership functions in the continuous blood pressure monitoring device.
Figure 15B:
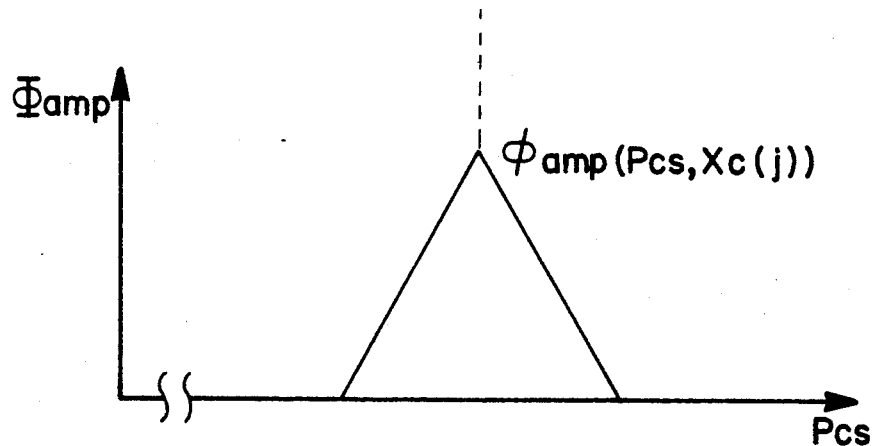

In ST 804, Xc(j) is linearly interpolated according to the following equation (16) as shown in FIGS. 15(a) and 15(b):

$$Xc(j) = Pcs(x - 1) - \{Pcs(x - 1) - Pcs(x)\} \times A \quad (16)$$

$$A = \frac{AMP(x - 1) - Vamp}{AMP(x - 1) - AMP(x)}$$

Further, the membership function $\phi amp(Pcs, Xc(j))$ is computed from this Xc(j) according to the following equation (17).

$$\phi amp(Pcs, Xc(j)) \doteq \quad (17)$$

$$\begin{bmatrix} 0 & [Pcs \leq Xc(j) - 10 \text{ mmHg}] \\ -0.1Pcs + 0.1Xc(j) + 1 & \\ & [Xc(j) - 10 \text{ mmHg} < Pcs \leq Xc(j)] \\ +0.1Pcs - 0.1Xc(j) + 1 & \\ & [Xc(j) < Pcs \leq Xc(j) + 10 \text{ mmHg}] \\ 0 & \\ & [Pcs > Xc(j) + 10 \text{ mmHg}] \end{bmatrix}$$

In other words, it is given as a triangle of equal sides symmetric about Xc(j) and having a base which is 20 mmHg in width.

In ST 806 j is incremented, and in ST 807 it is determined whether x has reached the maximum value of the relative cuff pressure Pcsmax. The program flow branches off to ST 802 if the determination result is NO, and to ST 808 if the determination result is YES.

As there may be two or more intersections, and there may be a plurality of membership functions $\phi amp(Pcs, Xc(1)), \ldots, \phi amp(Pcs, Xc(j))$, the membership function $\phi amp(Pcs)$ taking the largest value of all is computed (ST 808).

$$\Phi amp(Pcs) = MAX[\phi amp(Pcs, Xc(1)), \ldots, \phi amp(Pcs, Xc(j))] \quad (18)$$

In ST 809, 410 and 411, the membership functions $\Phi rav(Pcs)$, $\Phi wid(Pcs)$ and $\Phi con(Pcs)$ for the integrated level, the pulse wave width ratio and the degree of curving, respectively, are computed in the same manner as $\Phi amp(Pcs)$. For instance, if the characteristic functions for the amplitude AMP, the integrated level RAV, the pulse wave width ratio WID and the degree of curving CON are given as shown in FIGS. 13(a) through 13(d), respectively, and the results of short time measurement are given by Vamp, Vrav, Vwid and Vcon, the membership functions Φamp(Pcs), Φrav(Pcs), Φwid(Pcs) and Φcon(Pcs) are given as shown in FIGS. 12(a) through 12(d), respectively.

Now the process of logical computation is described in the following. The outline of this computation consists of computing Φ(Pcs) which gives rise to the minimum values of the membership functions Φamp(Pcs), Φrav(Pcs), Φwid(Pcs) and Φcon(Pcs), determining the relative cuff pressure Pcs which gives rise to the maximum value of Φ(Pcs), and determining the systolic blood pressure therefrom (refer to FIG. 12).

First of all, the pointer x is placed on the minimum value Pcsmin of the relative cuff pressure, and the initial value of Φmax is set to zero (ST 901, refer to FIG. 22). Then, x is incremented (ST 902), and the membership function Φ(x) is computed according to the following equation (19) (ST 903):

$$\Phi(x) = \text{MIN}[\phi amp(x), \phi rav(x), \phi wid(x), \phi con(x)] \quad (19)$$

In ST 904, it is determined if this Φ(x) is larger than Φmax. The program flow branches off to ST 906 if this determination result is NO, and to ST 905 if this determination result is YES. In ST 905, the value of x at this time point is set as xmax, and Φ(x) is set as Φmax. In ST 906, it is determined if x has reached the maximum value Pcs of the relative cuff pressure. If this determination result is NO the program flow branches off to ST 902, and if this determination result is YES the program flow branches off to ST 907. In ST 907, the systolic blood pressure SYS is computed according to the following equation (13):

$$SYS = \overline{Pc} + Xmax \quad (20)$$

where $\overline{Pc}$ is the cuff pressure detected during the short time measurement.

Thus, according to the third embodiment of the present invention, the time interval required for blood pressure measurement can be reduced, and it becomes possible to detect rapid changes in the blood pressure with the result that undue blockage of blood circulation of the patient can be avoided, an accurate blood pressure measurement is made possible, and failure of measurement due to insufficient pressurization can be avoided. Therefore, the advantages of the indirect measurement method in its simplicity of operation and high safety can be obtained.

Although the present invention has been described in terms of specific embodiments, it is possible to modify and alter details thereof without departing from the spirit of the present invention.

What is claimed is:

1. An electronic blood pressure meter, comprising:
a cuff adapted to be placed on a subject person;
pressure adjusting means for adjustably pressurizing air inside and cuff;
venting means for removing air from said cuff;
pressure detecting means for detecting air pressure in said cuff;
cardiovascular information detecting means for detecting cardiovascular information on said subject person from said pressure detecting means and computing a parameter from said cardiovascular information;
membership function storage means for storing a plurality of membership functions which relate a plurality of parameter values to a relative pressure of said air pressure in said cuff;
membership function selecting means selecting one of said membership functions corresponding to said computer parameter from said membership functions stored in said membership function storage means; and
control means for determining blood pressure of said person in accordance with the selected one of said membership functions.

2. An electronic blood pressure meter according to claim 1, wherein said cardiovascular information consists of a pulse wave of a subject person.

3. An electronic blood pressure meter according to claim 1, wherein said control means comprises blood pressure determining means for estimating said aforementioned relative pressure by carrying out an arithmetic operation on said membership function for said parameter selected by said membership function selecting means, and determining a blood pressure value.

4. An electronic blood pressure meter according to claim 1, wherein said control means comprises pressurization insufficiency detecting means for estimating said aforementioned relative pressure by carrying out a certain arithmetic operation on said selected membership function for said parameter, and detecting an insufficiency in cuff pressurization from this estimated relative pressure.

5. An electronic blood pressure meter according to claim 2, wherein said control means comprises
first blood pressure determining means for determining a blood pressure value according to said cardiovascular information obtained by said cardiovascular information detecting means and said air pressure detected by said pressure detecting means during said process of changing said air pressure in said cuff with said pressure adjusting means;
pulse wave parameter characteristics storage means for storing a relationship between a pulse wave parameter obtained by said cardiovascular information detecting means and a blood pressure value determined by said first blood pressure value determining means with respect to pulse wave detected by said cardiovascular information detecting means during a process of determining a blood pressure value with said first blood pressure determining means; and
second blood pressure determining means for computing said parameter with said cardiovascular information detecting means for one of a plurality of cycles of said pulse wave detected by said cardiovascular information detecting means after raising said air pressure in said cuff to a predetermined pressure value with said pressure adjusting means, comparing said parameter with an associated parameter stored in said pulse wave parameter characteristics storage means, and determining blood pressure values according to a predetermined logical operation on a result of said comparison.

* * * * *